(12) United States Patent
Shirai et al.

(10) Patent No.: US 11,680,286 B2
(45) Date of Patent: Jun. 20, 2023

(54) TAG-SEQUENCE-ATTACHED TWO-DIMENSIONAL CDNA LIBRARY DEVICE, AND GENE EXPRESSION ANALYSIS METHOD AND GENE EXPRESSION ANALYSIS APPARATUS EACH UTILIZING SAME

(71) Applicant: Hitachi, Ltd., Tokyo (JP)

(72) Inventors: Masataka Shirai, Tokyo (JP); Hideki Kambara, Tokyo (JP); Kiyomi Taniguchi, Tokyo (JP); Maiko Tanabe, Tokyo (JP)

(73) Assignee: Hitachi, Ltd., Tokyo (JP)

(*) Notice: Subject to any disclaimer, the term of this patent is extended or adjusted under 35 U.S.C. 154(b) by 58 days.

(21) Appl. No.: 17/323,311

(22) Filed: May 18, 2021

(65) Prior Publication Data
US 2021/0388422 A1  Dec. 16, 2021

Related U.S. Application Data

(62) Division of application No. 14/418,135, filed as application No. PCT/JP2012/069303 on Jul. 30, 2012, now Pat. No. 11,053,536.

(51) Int. Cl.
*C12Q 1/6837* (2018.01)
*C12N 15/10* (2006.01)

(52) U.S. Cl.
CPC ....... *C12Q 1/6837* (2013.01); *C12N 15/1096* (2013.01)

(58) Field of Classification Search
CPC ............ C12Q 1/6837; C12Q 2525/155; C12Q 2565/537; C12Q 2565/601; C12N 15/1096
See application file for complete search history.

(56) References Cited

U.S. PATENT DOCUMENTS

| 2005/0282190 A1 | 12/2005 | Shi et al. |
| 2006/0105380 A1 | 5/2006 | Slepnev |
| 2010/0105104 A1 | 4/2010 | Okano et al. |

(Continued)

FOREIGN PATENT DOCUMENTS

| JP | 2010-46073 A | 3/2010 |
| WO | WO 03/035841 A2 | 5/2003 |

(Continued)

OTHER PUBLICATIONS

International Search Report dated Oct. 30, 2012 with English translation (four (4) pages).

(Continued)

*Primary Examiner* — Young J Kim
(74) *Attorney, Agent, or Firm* — Crowell & Moring LLP

(57) ABSTRACT

The present invention relates to a method, a device, and an apparatus for analyzing the expression of a gene in single cells. Specifically, the present invention relates to: a device for gene expression analysis, characterized by including a support, in which a nucleic acid probe having a test nucleic acid capture sequence and a known sequence, and further containing a cell recognition tag sequence which differs depending on the difference in position on the surface of the support or in the vicinity of the surface thereof, and a common primer sequence having a known sequence is two-dimensionally distributed and immobilized on the surface of the support or in the vicinity of the surface thereof; and a method and an apparatus using the device for gene expression analysis.

6 Claims, 15 Drawing Sheets

Specification includes a Sequence Listing.

(56) References Cited

U.S. PATENT DOCUMENTS

2010/0240550 A1   9/2010   Jackson
2012/0245053 A1   9/2012   Shirai et al.
2014/0155274 A1   6/2014   Xie et al.

FOREIGN PATENT DOCUMENTS

WO    WO 2011/068088 A1    6/2011
WO    WO 2012/140224 A1    10/2012

OTHER PUBLICATIONS

Islam et al., "Characterization of the single-cell transcriptional landscape by highly multiplex RNA-seq," Genome Research, May 4, 2011, Cold Spring Harbor Laboratory Press (twenty-four (24) pages).

Kivioja et al., "Counting absolute numbers of molecules using unique molecular identifiers," Nature Methods, Jan. 2012, pp. 72-76, vol. 9, No. 1, Nature America, Inc. (five (5) pages).

Smith et al., "Highly-multiplexed barcode sequencing: an efficient method for parallel analysis of pooled samples," Nucleic Acids Research, May, vol. 38, No. 13, e142, pp. 1-7, 2010.

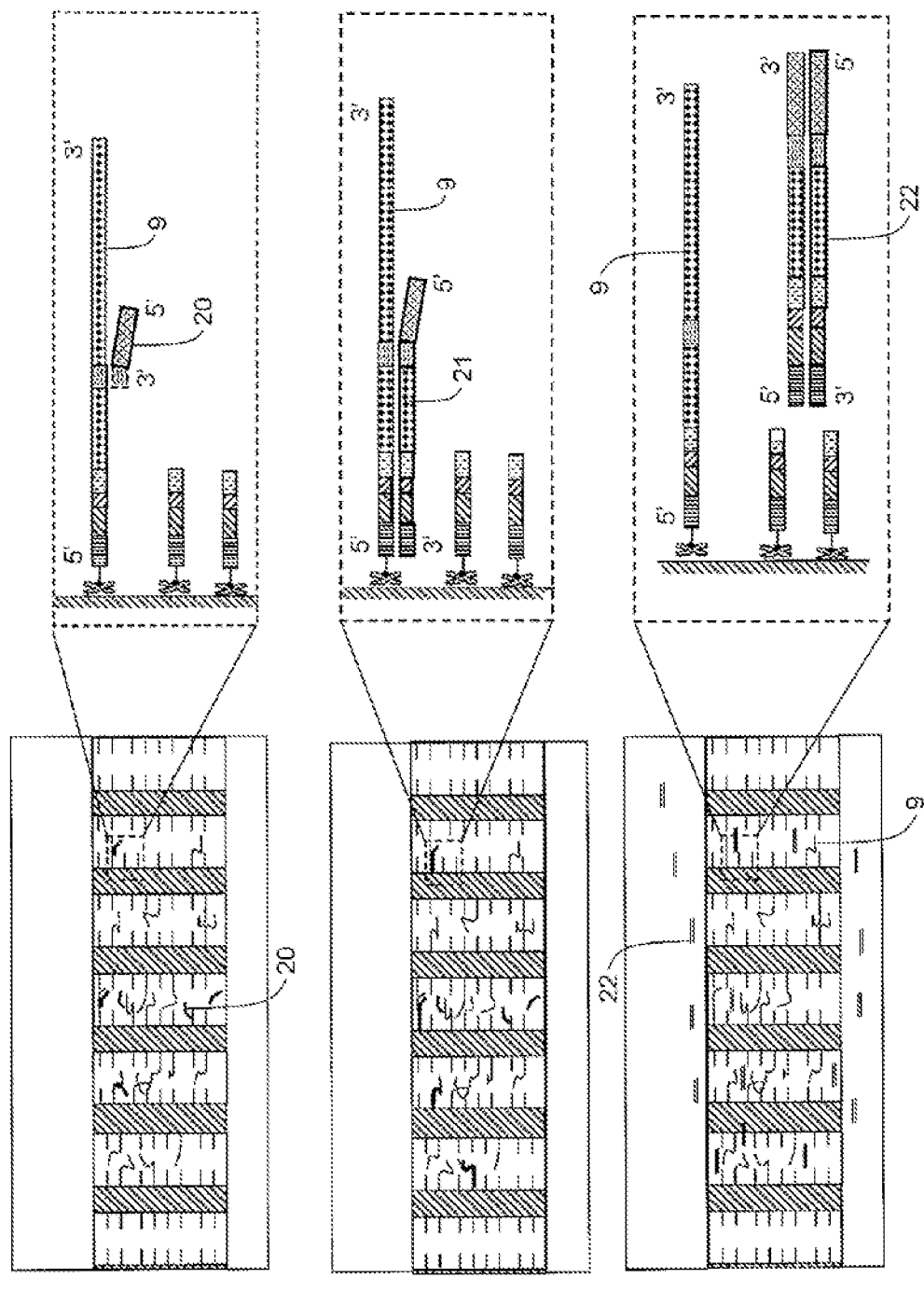

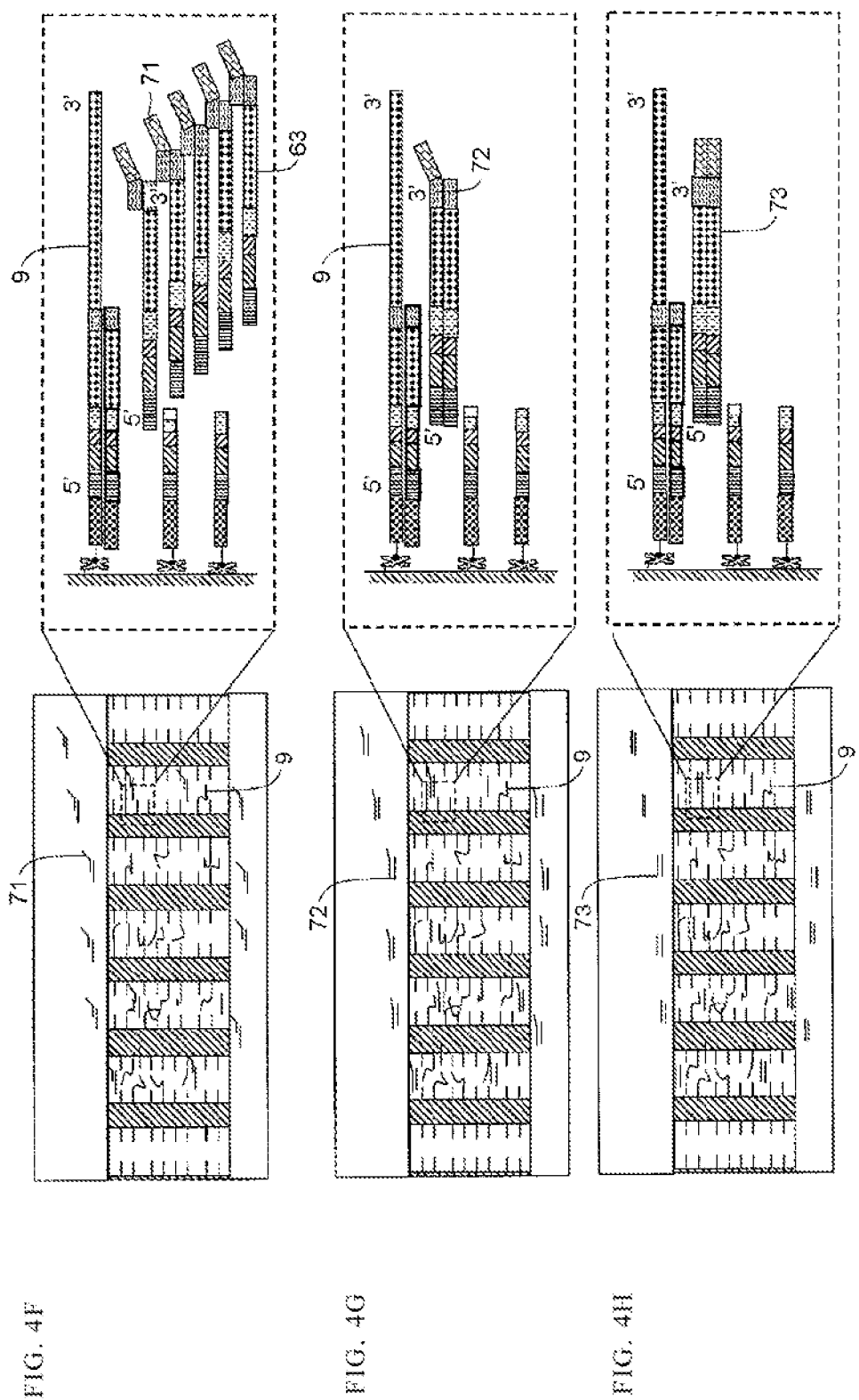

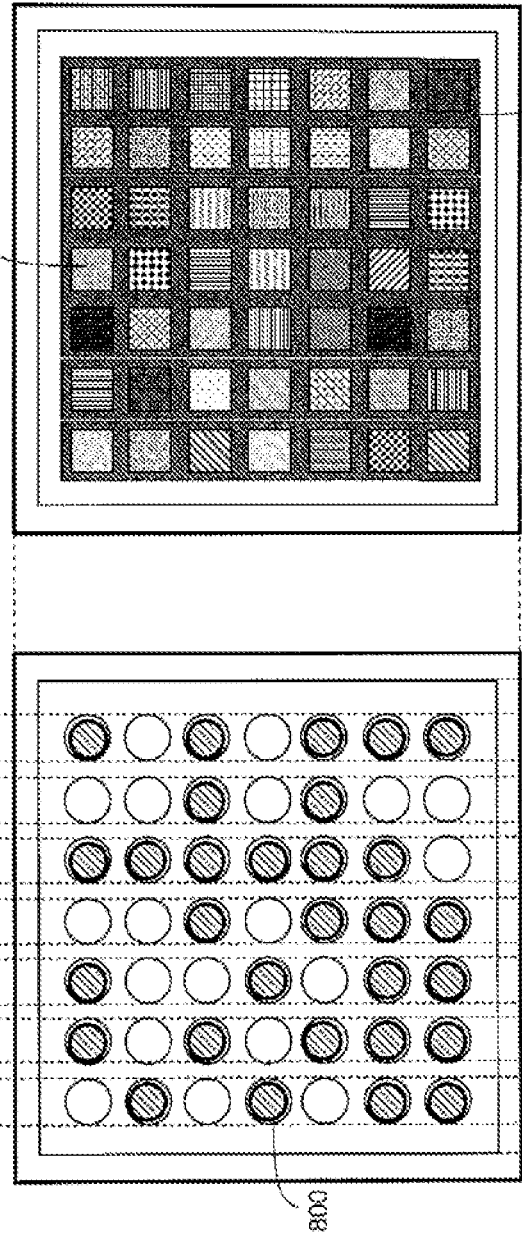
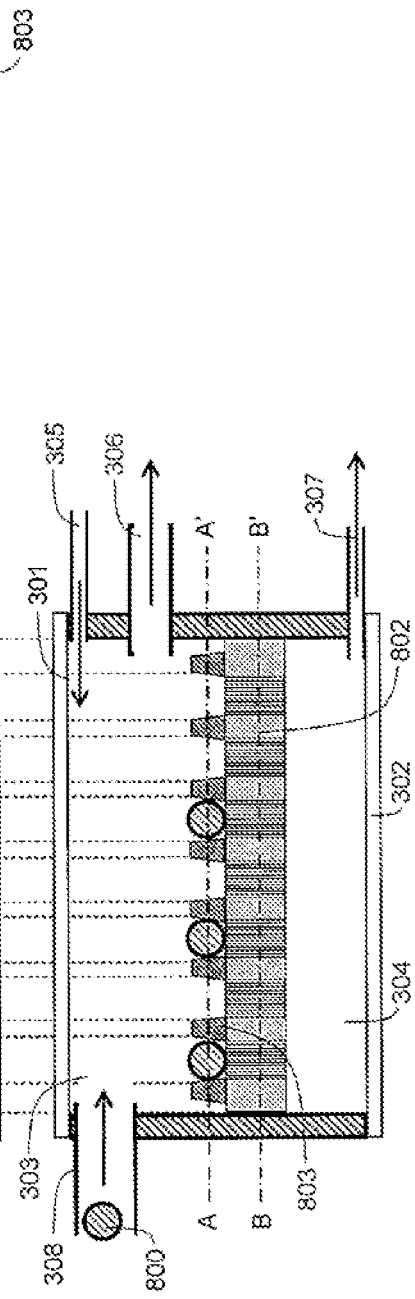
FIG. 5C
FIG. 5B
FIG. 5A

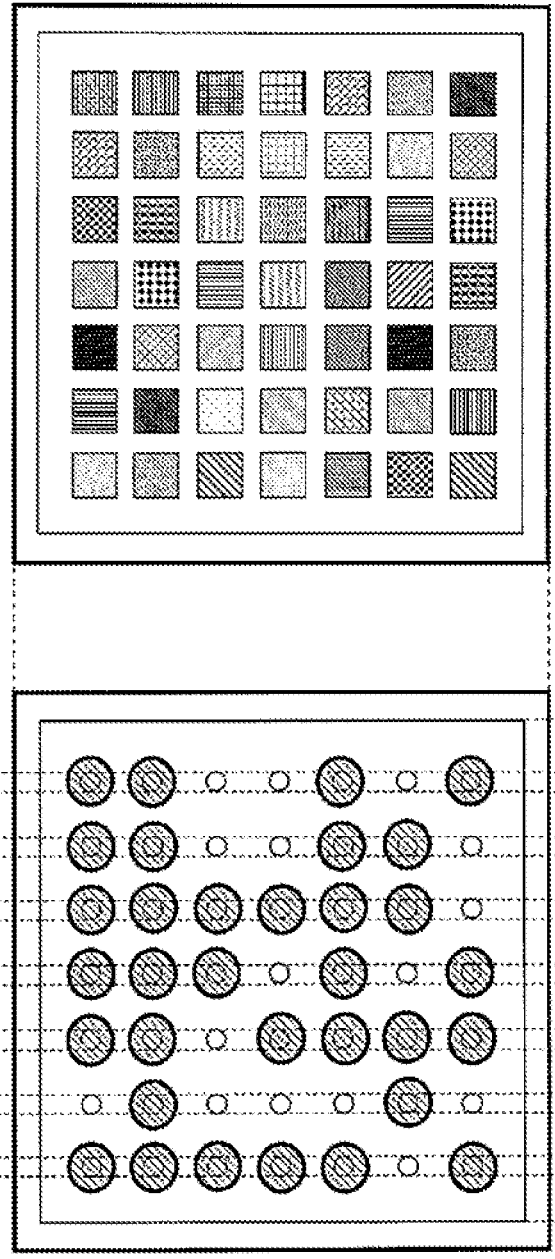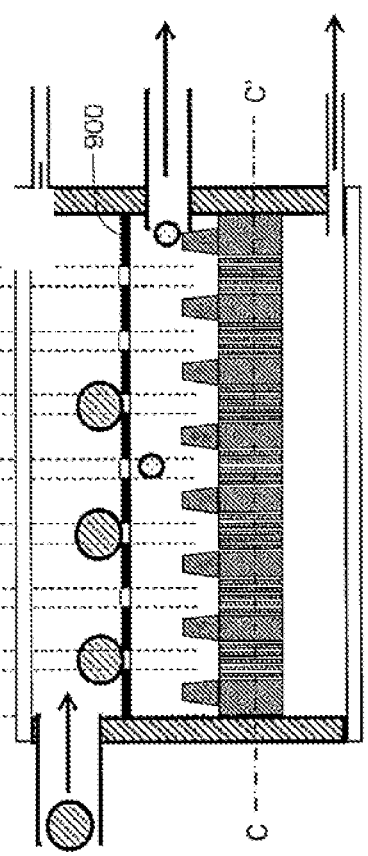
FIG. 6C
FIG. 6B
FIG. 6A

TAG-SEQUENCE-ATTACHED TWO-DIMENSIONAL CDNA LIBRARY DEVICE, AND GENE EXPRESSION ANALYSIS METHOD AND GENE EXPRESSION ANALYSIS APPARATUS EACH UTILIZING SAME

CROSS REFERENCE TO RELATED APPLICATIONS

This application is a divisional of U.S. patent application Ser. No. 14/418,135, filed Jan. 29, 2015, which is a national stage of International Application No. PCT/JP2012/069303 filed Jul. 30, 2012, the entire contents of which are hereby incorporated by reference.

TECHNICAL FIELD

The present invention relates to a method, a device, and an apparatus for analyzing the expression of a gene in individual cells.

BACKGROUND ART

In gene expression analysis, a method in which mRNA is extracted from a group of cells, cDNA, which is a complementary strand thereto, is prepared, the prepared cDNA is amplified by PCR or the like to increase the number of copies thereof, and thereafter a target is captured at a position of a corresponding probe using a DNA probe array (DNA chip) and fluorescently detected has been used. However, in such a method using PCR amplification and a DNA chip, the accuracy of quantitative analysis is low, and thus, a highly accurate gene expression profile analysis method has been demanded. Recently, a method of performing quantitative analysis by extracting mRNA from a single cell has been demanded. As an analysis method with high quantitatively, quantitative PCR is known. In this method, quantitative analysis is performed by preparing a reference sample having the same DNA sequence as that of a target, performing PCR amplification under the same conditions, and monitoring and comparing the progress of amplification with a fluorescent probe. However, when the target is a single cell, the number of mRNAs originally present is small, and therefore, it is difficult to perform quantitative analysis. In addition, in order to quantitatively analyze the expression of multiple genes, it is necessary to divide a sample into portions and quantitatively analyze each portion independently. If the number of target genes is large and genes with low expression level are included, some genes may not be able to be measured due to the division of the sample.

Under such circumstances, the research group of the present inventors invented a method in which all mRNAs are converted to cDNAs and retained on beads to prepare a cDNA library (a cDNA assembly containing all cDNAs), which is used in quantitative analysis. It was shown that according to this method, by repeatedly using the cDNA library, a measurement error of a gene with low expression level due to division of a sample is eliminated, and thus, the expression levels of multiple genes contained in a single cell can be accurately measured.

Further, a method in which a small amount of mRNA in a single cell is converted to cDNA by reverse transcription, nucleic acid amplification is performed using PCR amplification, then, the amplification product is sequenced using a large-scale DNA sequencer, the sequencing results are summed up, and the number of nucleic acid sequences after amplification is counted, thereby estimating the number of mRNA molecules is coming into use (NPL 1). In this method, the upper limit of the number of genes which can be measured is determined by the number of rows in the large-scale DNA sequencer, and therefore, it is possible not only to measure all of 20,000 and several thousand genes, but also, in principle, to measure one hundred thousand sequences including splicing variants by counting. Further, cells are inserted one by one into each of multiple reaction tanks, and a tag sequence for discriminating cells is introduced as a reagent into a liquid phase in the reaction tanks, and after PCR amplification, amplification products thereof are all together subjected to sequence analysis using a large-scale DNA sequencer. However, with reference to the tag sequence at this time, cells in which the sequenced amplification products were originally present can be identified (NPL 1).

On the other hand, when PCR amplification is performed, there exists a problem of amplification bias in which amplification efficiency differs among genes. In NPL 2, a method in which a random sequence is introduced when reverse transcription from mRNA is performed and the influence of PCR bias occurring during PCR amplification performed after the introduction of the random sequence is excluded by performing sequence analysis of the sequence thereof and a target cDNA at the same time has been proposed (NPL 2).

CITATION LIST

Non Patent Literature

NPL 1: Islam, S. et al., Genome Research Vol. 21, No. 7, pp. 1160-1167, 2011

NPL 2: Kivioja, T. et al., Nature Methods, Vol. 9, No. 1, pp. 72-74, 2011

SUMMARY OF INVENTION

Technical Problem

As described above, it has been demanded that the contents of cells constituting a tissue be quantitatively analyzed one by one and the expression levels of various genes be quantitatively monitored while keeping two-dimensional information in the tissue.

In the above-mentioned method for determining the expression levels of multiple genes by repeatedly performing quantitative determination of a cDNA library on beads, the frequency of measurement operations which can be repeated is limited to about 10 to 20 times, and therefore, the number of genes which can be measured is limited to some extent. On the other hand, in the method using a large-scale DNA sequencer after reverse transcription and PCR amplification, although the number of genes to be measured can be sufficiently increased, in general, the nucleic acid amplification factor differs among genes and reproducibility of the amplification factor is low. Further, the number of cells which can be measured simultaneously is about 100 or less, and also the cost of necessary reagents is also very high.

Further, in either method, in order to realize gene expression analysis in a single cell, it is necessary to isolate cells once, introduce the cells into reaction wells separately, and dispense reagents for cell disruption, reverse transcription, and also PCR amplification in each reaction well. Due to this, in order to analyze a large number of cells, a robot for such a dispensing operation is needed, and the analysis apparatus becomes larger and expensive. In addition, in order to eliminate the dispensing operation by a robot, when extracting mRNA from individual cells and performing nucleic acid amplification using microfluidics, it is necessary to arrange reaction mixture channels in rows. Therefore, a chip size increases in proportion to the number of rows, and thus, the size of the microfluidics device becomes larger and its price increases.

When a cDNA library sheet is used for realizing gene expression analysis of a large number of cells at a time at low cost, it is possible to measure a large number of cells at a time. However, it was necessary to repeatedly use the cDNA library for increasing the number of genes which can be analyzed. Therefore, there was a limitation on the number of genes to be analyzed.

Therefore, an object of the present invention is to provide a method and a means for performing gene expression analysis with respect to a gene expressed in multiple cells constituting a biological tissue while keeping the positional information of the cells at a single cell level.

Solution to Problem

In order to achieve the above-mentioned object, the present invention provides a gene expression analysis method including: a step of hybridizing a test nucleic acid to serve as a target to a nucleic acid probe in a support in which the nucleic acid probe having a test nucleic acid capture sequence and a known sequence, and further containing a cell recognition tag sequence which differs depending on the difference in position on the surface of the support or in the vicinity of the surface thereof is two-dimensionally distributed and immobilized on the surface of the support or in the vicinity of the surface thereof; a step of synthesizing a complementary DNA strand to the test nucleic acid, thereby preparing a cDNA library constituted by the DNA complementary strand containing the tag sequence; and a step of performing nucleic acid amplification of the whole or part of the cDNA library. Further, the present invention provides a device and an apparatus for performing the method.

Advantageous Effects of Invention

According to the invention, a method, a device, and an apparatus for performing gene expression analysis are provided. For example, in the invention, a cDNA library can be prepared while keeping the positional information of cells in a tissue by converting mRNA of a gene expressed in all cells in a biological tissue to cDNA, and therefore, the expression of a gene at an arbitrary site of interest or the expression of a gene at all sites can be known. According to this, a variety of information which could not be obtained so far, for example, how the gene information is transferred in a tissue, and so on can be visualized. Due to this, for example, according to the invention, a lot of new information such as the flow of gene information in cells or tissues, and the influence of stimulation on tissues can be obtained. Accordingly, the invention is useful in the fields of gene expression analysis, cell functional analysis, a biological tissue analysis method, disease investigation and diagnosis method, drug development, and the like.

Objects, configurations, and effects other than those described above will be apparent through the following description of embodiments.

BRIEF DESCRIPTION OF DRAWINGS

FIGS. 1C-1E are views showing one example of the method of the invention and a configuration example and a use mode of a device for gene expression analysis (a pore array sheet) to be used.

FIGS. 4F-4H are views showing another example of the method of the invention and a configuration example and a use mode of a device for gene expression analysis (a pore array sheet) to be used.

FIGS. 5A-5C are views showing a transverse section and a cross section of one example of a device for preparing a cell array.

FIGS. 6A-6C are views showing a transverse section and a cross section of another example of a device for preparing a cell array.

DESCRIPTION OF EMBODIMENTS

Figures 1A, 1B:
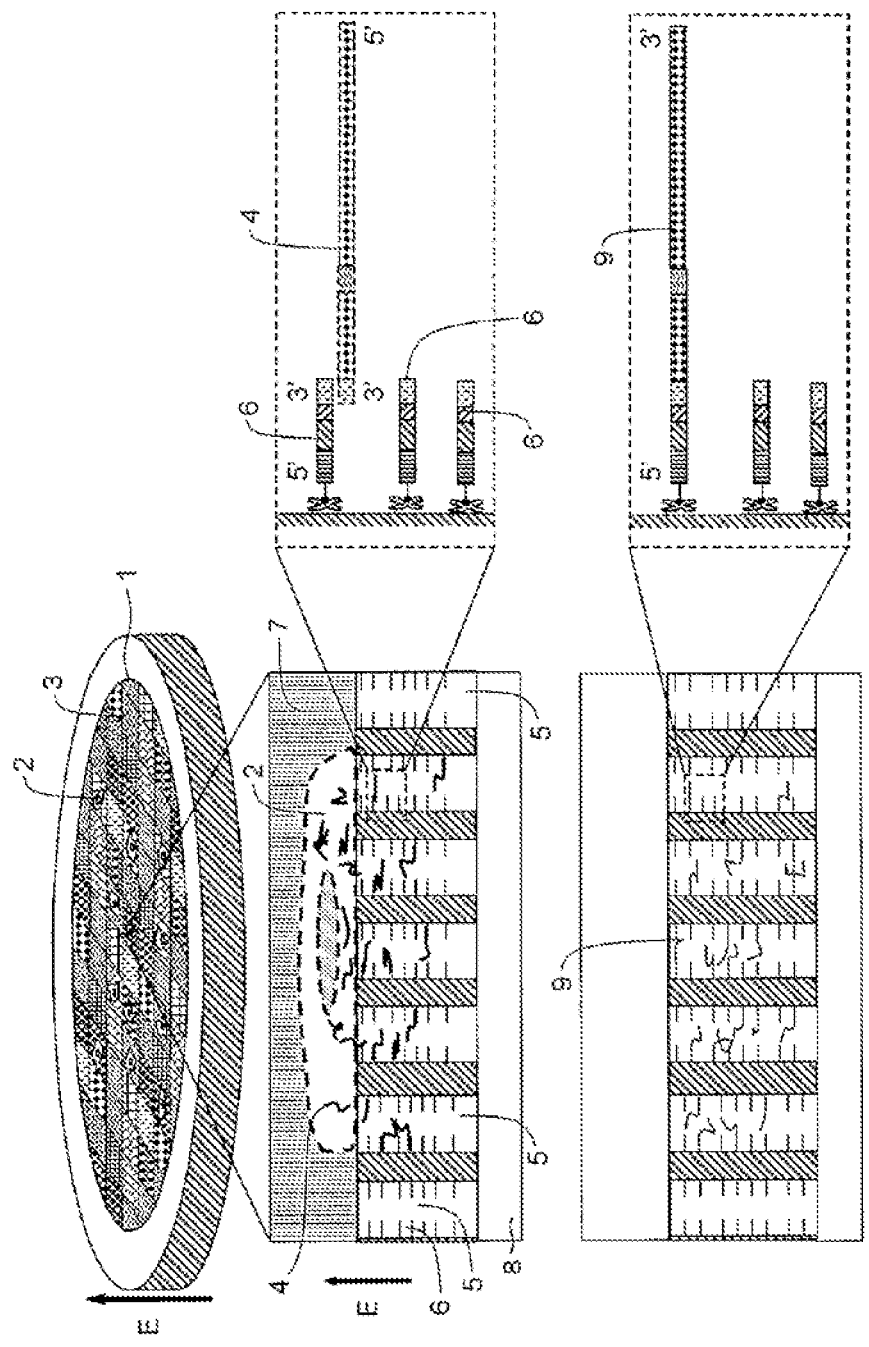
FIGS. 1A and 1B are views showing one example of a method of the invention and a configuration example and a use mode of a device for gene expression analysis (a pore array sheet) to be used.

In the invention, a cDNA library sheet is prepared from a test nucleic acid (for example, mRNA) while keeping the two-dimensional cell distribution information in a biological tissue. At this time, in order to make a known tag sequence (a sequence for discriminating positions or regions on the cDNA library sheet) be included in a sequence of some amplification products also after the amplification products obtained in the nucleic acid amplification step thereafter are released from the cDNA library sheet, a nucleic acid probe containing the known tag sequence and a sequence for capturing a test nucleic acid is immobilized on the surface of a device (support) for preparing the cDNA library sheet or in the vicinity of the surface thereof. At this time, in the nucleic acid probe, a common primer sequence for amplification to be used in the nucleic acid amplification step may be disposed on the 5'-terminal side from the tag sequence. The gene expression level is determined by sequencing the amplification product obtained by the nucleic acid amplification step from the cDNA library or by quantitatively determining the amplification product by optical measurement such as fluorescence measurement. At this time, the information of the simultaneously obtained tag sequence can be acquired, and therefore, the expression level of a specific gene can be determined for each position or region on the cDNA library sheet. When sequencing is used in the quantitative determination, a large number of genes determined according to the number of rows can be quantitatively determined. Further, also when fluorescence measurement is performed, by performing the nucleic acid amplification step, high fluorescence detection sensitivity is not needed, and therefore, the types of fluorescent substances which can be used increases, and also it becomes easy to use multiple fluorescent substances in combination, and at the same time, the number of genes which can be discriminated can be increased.

Accordingly, the gene expression analysis method according to the invention includes the following steps:

a step of hybridizing a test nucleic acid to serve as a target to a nucleic acid probe in a support in which the nucleic acid probe having a test nucleic acid capture sequence and a known sequence, and further containing a cell recognition tag sequence which differs depending on the difference in position on the surface of the support or in the vicinity of the surface thereof is two-dimensionally distributed and immobilized on the surface of the support or in the vicinity of the surface thereof;

a step of synthesizing a complementary DNA strand to the test nucleic acid, thereby preparing a cDNA library constituted by the DNA complementary strand containing the tag sequence; and a step of performing nucleic acid amplification of the whole or part of the cDNA library.

The "gene expression analysis" or "biomolecule expression analysis" as used herein means that the expression of a gene or a biomolecule, in other words, a test nucleic acid to serve as a target in a sample (individual cells, a tissue section, or the like) is quantitatively analyzed, the expression distribution of a gene (a test nucleic acid) or a biomolecule in a sample is analyzed, or the data of correlation between a specific position in a sample and the expression level of a gene (a test nucleic acid) or a biomolecule is obtained.

The sample is not particularly limited as long as it is a sample derived from a living organism whose gene expression is to be analyzed, and an arbitrary sample such as a cell-sample, a tissue sample, or a liquid sample can be used. Specifically, a sample composed of a single cell, a sample containing multiple cells, a tissue section sample, a sample in which multiple individual cells are arranged in an array retained two-dimensionally.

Further, the living organism from which a sample is derived is not particularly limited, and a sample derived from an arbitrary living organism such as a vertebrate (for example, a mammal, a bird, a reptile, a fish, an amphibian, or the like), an invertebrate (for example, an insect, an eelworm, a crustacean, or the like), a protist, a plant, a fungus, a bacterium, or a virus can be used.

As the test nucleic acid to serve as a target in the method of the invention, messenger RNA (mRNA), noncoding RNA (ncRNA), microRNA, DNA, and fragments thereof can be used. For example, nucleic acids contained in a sample are extracted and the test nucleic acid can be prepared by a known method in the art. For example, cells are lysed using a protease such as Proteinase K, a chaotropic salt such as guanidine thiocyanate or guanidine hydrochloride, a surfactant such as Tween or SDS, or a commercially available cell lysis reagent, and nucleic acids, that is, DNA and RNA contained therein can be eluted. When mRNA is used as the test nucleic acid, by degrading DNA among the nucleic acids eluted by the cell lysis described above with a DNA nuclease (DNase), a sample containing only RNA as the test nucleic acid can be obtained.

In the invention, specific examples of the test nucleic acid to serve as a target include, although not limited thereto, mRNA in individual cells constituting a biological tissue and mRNA in multiple cells arranged in an array retained two-dimensionally.

The nucleic acid probe to be used contains at least a sequence capable of capturing the test nucleic acid to serve as a target (herein referred to as "test nucleic acid capture sequence") and a sequence which differs depending on the difference in position or region in the support (herein referred to as "cell recognition tag sequence").

The test nucleic acid capture sequence is not particularly limited as long as it can hybridize the test nucleic acid to serve as a target and capture it, and can be appropriately designed by those skilled in the art by consideration of the type and sequence of the test nucleic acid. For example, in the case where the test nucleic acid to serve as a target is mRNA, a poly T sequence is preferably used as the test nucleic acid capture sequence. The nucleic acid probe containing a poly T sequence, that is, an oligo (dT) can be synthesized by a conventional method, and the polymerization degree of the oligo (dT) may be any as long as the oligo(dT) can hybridize the poly A sequence of mRNA to capture the mRNA on the support having the nucleic acid probe containing the oligo (dT) immobilized thereon, and can be set to, for example, about 10 to 30 bases, about 10 to 20 bases, or about 10 to 15 bases. Further, it is preferred to add a 2-base random sequence to the oligo(dT) sequence at the 3' end thereof. According to this, the amount of artifacts when synthesizing a complementary DNA strand can be largely reduced. Examples of such a random sequence include a VN sequence (V denotes A or G or C, and N denotes A or G or C or T). Further, for example, when the test nucleic acid to serve as a target is microRNA or genomic DNA, as the test nucleic acid capture sequence, a random sequence or a complementary sequence to part of the test nucleic acid to serve as a target can be used.

The cell recognition tag sequence can be made to include a known sequence having an arbitrary length. For example, by using a 5-base known sequence, $4^5$ (1024) types of different cell recognition tag sequences can be prepared. Further, for example, by using a 10-base known sequence, $4^{10}$ types of different cell recognition tag sequences can be prepared. Therefore, the length of the cell recognition tag sequence is determined according to the number of positions or regions on the support to be discriminated so that different cell recognition tag sequences capable of discriminating them can be prepared. Specifically, the length thereof is preferably set to 5 to 30 bases, 5 to 20 bases, 5 to 15 bases, or 5 to 10 bases.

The nucleic acid probe may further contain a molecule recognition tag sequence. The molecule recognition tag sequence is not particularly limited as long as it has a random sequence with a given length (for example, 5 to 30 bases, preferably 10 to 20 bases, more preferably 10 to 15 bases), and may have a known sequence or may have an unknown sequence. In the nucleic acid amplification step performed later, when amplification is performed on the support having a particularly large volume (a porous sheet, beads, or the like), amplification efficiency bias occurs depending on the length or the sequence structure of the test nucleic acid to be amplified, the position where the test nucleic acid exists, or the like. By using the molecule recognition tag sequence, amplification bias in the nucleic acid amplification step is corrected, and thus, accurate quantitative determination can be performed. As a specific molecule recognition tag sequence, for example, random sequences represented by SEQ ID NOS: 25 to 29 can be used.

Further, the nucleic acid probe may further contain a common primer sequence (a common sequence for amplification). The common primer sequence is not particularly limited as long as it has a known sequence with an appropriate length for performing nucleic acid amplification. Such a common primer sequence can be appropriately designed by those skilled in the art. For example, the length of the common primer sequence can be set to 10 to 50 bases, 15 to 50 bases, 15 to 40 bases, 15 to 30 bases, or 15 to 20 bases. By adding such a common primer sequence to the nucleic acid probe, an amplification reaction in the nucleic acid amplification step later can be conveniently performed.

As described below, in the nucleic acid amplification step, when a transcription reaction from cDNA to cRNA is performed by a transcription factor, the nucleic acid probe preferably further contains a transcription factor promoter sequence. As such a promoter sequence, T7 is used, however, additional examples thereof include SP6 and T3. In the amplification of the nucleic acid, the activity of T7 RNA polymerase, SP6 RNA polymerase, or T3 RNA polymerase is used. The transcription factor promoter sequence to be added to the nucleic acid probe can be selected according to the type of the transcription factor to be used. For example, when T7 RNA polymerase is used as the transcription factor, a T7 promoter sequence (specifically, for example, a sequence represented by base numbers 1 to 42 of SEQ ID NO: 24) can be added to the nucleic acid probe. The nucleic acid amplification using the transcription factor promoter sequence is isothermal amplification, and therefore, not only a temperature controller for applying a thermal cycle is not needed, but also the possibility that the probe DNA immobilized on the surface of the device is detached at high temperatures can be decreased.

The sites of the test nucleic acid capture sequence and the cell recognition tag sequence in the nucleic acid probe, and if existing, the site (s) of the molecule recognition tag sequence and/or the common primer sequence and/or the transcription factor promoter sequence can be easily understood and designed by those skilled in the art.

In the invention, the nucleic acid probe is two-dimensionally distributed and immobilized on the surface of the support or in the vicinity of the surface thereof in advance. According to this, gene information from the test nucleic acid derived from respective cells can be obtained without damaging cells or tissues containing the test nucleic acid (or biomolecule) to serve as a target, or using a robot or the like. In particular, since the cells or tissues are not damaged, a change in gene expression derived from the damage can be avoided.

The support to be used is not particularly limited as long as it is prepared from a material generally used for preparing a cDNA library in the art. Examples of the support include a sheet, a membrane, a gel thin film, a capillary plate, beads and a film. Examples of the material thereof include metals such as gold, silver, copper, aluminum, tungsten, molybdenum, chromium, platinum, titanium, and nickel; alloys such as stainless steel; silicon; glass materials such as glass, quartz glass, fused quartz, synthetic quartz, alumina, and photosensitive glass (these materials are basically transparent); plastics such as a polyester resin, polystyrene, a polyethylene resin, a polypropylene resin, an ABS resin (Acrylonitrile Butadiene Styrene resin), nylon, an acrylic resin, and a vinyl chloride resin (these materials a generally not transparent, but are preferably made transparent for enabling optical measurement); agarose, dextran, cellulose, polyvinyl alcohol, nitrocellulose, chitin, and chitosan. For example, if a sheet is used as the support, the sheet can be prepared from, for example, alumina, glass, or the like. Further, if a gel thin film is used as the support, the gel thin film can be prepared from, for example, an acrylamide gel, gelatin, modified polyethylene glycol, modified polyvinylpyrrolidone, a hydro gel, or the like. If a membrane is used as the support, for example, cellulose acetate, nitrocellulose, a membrane formed of a mixture thereof, a nylon membrane, or the like can be used. If beads are used as the support, beads can be prepared from a resin material (polystyrene or the like), an oxide (glass or the like), a metal (iron or the like), Sepharose, a combination thereof, or the like. In particular, from the viewpoint of convenience of operation, magnetic beads are preferably used. In an embodiment, the support is preferably formed from a transparent material with respect to a light with a wavelength in at least part of the wavelength range of 300 nm to 10000 nm. According to this, analysis of gene expression can be optically performed on the support.

Here, the support preferably has multiple microspaces divided two-dimensionally so that cDNA can be retained while keeping the two-dimensional positional information in the cDNA library. For example, by providing pores in a sheet, a gel thin film, or a capillary plate (so as to have a porous structure), by using a porous sheet, or by spreading beads in divided spaces such as cells, such multiple microspaces can be provided. In an embodiment, multiple through-holes are two-dimensionally provided for the support in the vertical direction, and the nucleic acid probe is immobilized on at least the inner walls of the through-holes, and the cell recognition tag sequence in the nucleic acid probe is made different depending on the position in the through-hole. The reason why such a configuration is adopted is because when the cell is disposed on the support, the area immediately below the cell is required to be an area usable for capturing the test nucleic acid (for example mRNA), however, the area on the surface of the support is not sufficient for capturing all test nucleic acids (for example mRNA), and it is necessary to increase the surface area of the support immediately below the cell. On the other hand, in the case where a cDNA library is prepared using the support having an increased surface area by providing multiple microspaces, when a product obtained by the nucleic acid amplification step is taken out of the support and sequence analysis or the like is performed, a probability that the amplification product from an internal portion of the support is nonspecifically adsorbed on the surface of the support is lower than the amplification product from the vicinity of the surface of the support, and thus, bias occurs in the amplification products. In the invention, in order to solve this problem, the molecule recognition tag sequence as described above is introduced into the nucleic acid probe. According to this, when sequence analysis of the amplification products is performed, it is found that the amplification products having the same molecule recognition tag sequence are the same molecules before the nucleic acid amplification step, and therefore, bias occurring in the amplification step can be offset. The interval between the microspaces in such a support is preferably a size corresponding to a single cell or smaller than the size of the cell.

The immobilization of the nucleic acid probe on the support can be performed according to any method known in the art. For example, the nucleic acid probe can be immobilized on the surface of the support, the internal portions of pores, membrane fibers, the surfaces of beads, or the like by employing covalent bonding, ionic bonding, physical adsorption, or biological binding (for example, binding between biotin and avidin or streptoavidin, binding between an antigen and an antibody, or the like). Further, it is also possible to immobilize the nucleic acid probe on the support through a spacer sequence.

The immobilization of the nucleic acid probe on the support through a covalent bond can be achieved by, for example, introducing a functional group into the nucleic acid probe and also introducing a functional group reactive to this functional group into the surface of the support, and allowing both functional groups to react with each other. For example, a covalent bond can be formed by introducing an amino group into the nucleic acid probe and introducing an active ester group, an epoxy group, an aldehyde group, a carbodiimide group, an isothiocyanate group, or an isocyanate group into the support. Alternatively, a mercapto group may be introduced into the nucleic acid probe and an active ester group, a maleimide group, or a disulfide group may be introduced into the support. As one of the methods for introducing a functional group into the surface of the support, a method of treating the support with a silane coupling agent having a desired functional group may be used. As an example of the coupling agent, γ-aminopropyltriethoxysilane, N-β-(aminoethyl)-γ-aminopropyltrimethoxysilane, N-β-(aminoethyl)-β-aminopropylmethyldimethoxysilane, or the like can be used. As another method for introducing a functional group serving as a binding site into the support, a plasma treatment can be used. Further, examples of the method for immobilizing the nucleic acid probe on the support by physical adsorption include a method of electrostatically binding the nucleic acid probe to the support surface-treated with a polycation (polylysine, polyallyl amine, polyethylene imine, or the like) by utilizing a charge of the nucleic acid probe.

Incidentally, it is preferred to perform surface coating of the support so that other substances (nucleic acids, proteins, and the like) are not adsorbed thereon.

In the method of the invention, for example, the test nucleic acid to serve as a target is mRNA in individual cells constituting a biological tissue, and the cell recognition tag sequence is made to include a sequence which differs per region smaller than the size of the cell, whereby a cDNA library can be prepared while keeping the in-plane positional information of the cell constituting the biological tissue. According to this, the difference in gene expression in the cell or among the cells constituting the biological tissue can be analyzed. Here, for example, in the case where the biological tissue is a tissue section, by transferring mRNA in individual cells constituting the tissue section to the support having the nucleic acid probe containing the cell recognition tag sequence which differs per region immobilized thereon, a cDNA library can be prepared while keeping the in-plane positional information of the cell constituting the tissue section. According to this, the difference in gene expression among multiple cells can be analyzed.

Alternatively, in the method of the invention, for example, the test nucleic acid to serve as a target is mRNA in multiple cells arranged in an array retained two-dimensionally, and the cell recognition tag sequence is made to include a sequence which differs per cell, whereby the cDNA library can be prepared while keeping the positional information of the multiple cells.

In order to hybridize the test nucleic acid in a sample such as individual cells or a tissue with the nucleic acid probe immobilized on the support, the test nucleic acid in the sample is extracted as described above and brought into contact with the support. At this time, it is also possible to use, for example, a method in which an electric field is applied to the sample containing the test nucleic acid and the support and the test nucleic acid is transferred to the vicinity of the nucleic acid probe immobilized on the support by electrophoresis by utilizing the negative charge of the nucleic acid.

The hybridization reaction can be performed by incubating the support having the nucleic acid probe immobilized thereon and the test nucleic acid. The incubation for such hybridization is performed at a temperature of 70° C. for about 5 minutes while gently stirring, and thereafter, the temperature is preferably decreased gradually to room temperature at about 0.1° C./sec. After the hybridization reaction, reagents and unbound components are preferably washed off from the support.

After the test nucleic acid and the nucleic acid probe are hybridized, a complementary DNA strand (cDNA) to the sequence of the test nucleic acid or part thereof is synthesized. The complementary strand can be synthesized by a known method in the art. For example, when the test nucleic acid is RNA such as mRNA, cDNA can be synthesized by, for example, a reverse transcription reaction using a reverse transcriptase. Further, when the test nucleic acid is DNA, cDNA can be synthesized by, for example, a replication reaction using a polymerase. After the synthesis reaction, the test nucleic acid is degraded and removed using, for example, RNase. As a result, a cDNA library constituted by the tag sequence and cDNA corresponding to the test nucleic acid is prepared in the support. In the thus prepared cDNA library, cDNA is preferably retained in multiple microspaces two-dimensionally divided in the support.

After synthesis of cDNA, by performing a washing-off operation for the cDNA library (support), residual reagents, for example, a cell-lysis reagent and DNA nuclease can be removed, and thus, the nucleic acid amplification step thereafter can be performed without being inhibited.

The cDNA library prepared as described above can be repeatedly used by washing after the respective operations, and by using the same cDNA library, the nucleic acid amplification step or the gene expression detection (for example, sequencing) step described below can be performed plural times.

Further, optionally, by transferring cDNA contained in the cDNA library prepared as described above or by producing a nucleic acid fragment corresponding to cDNA contained in the cDNA library, information of cDNA contained in the original cDNA library can be transferred to a liquid phase.

Subsequently, nucleic acid amplification of the whole or part of the cDNA library prepared as described above is performed. In the nucleic acid amplification step, first, a primer containing a sequence specific to a gene to be analyzed for gene expression (herein also referred to as "gene-specific sequence") is annealed to cDNA retained in the cDNA library, whereby a cDNA strand containing the sequence of part of the test nucleic acid and the sequence contained in the nucleic acid probe described above is produced. At this time, for the primer, by using a sequence present at a specific distance from the 3' end of the gene to be analyzed as the gene-specific sequence, the sizes of the amplification products obtained in the nucleic acid amplification step can be averaged when multiple genes are analyzed. Further, by adding a common primer sequence corresponding to the common primer sequence contained in the nucleic acid probe described above (for example, a common reverse primer sequence corresponding to a common forward primer sequence contained in the nucleic acid probe) to the primer, it becomes possible to conveniently and efficiently perform the subsequent nucleic acid amplification reaction.

As the nucleic acid amplification reaction, any method known in the art can be used. Examples thereof include a polymerase chain reaction (PCR), a Nucleic Acid Sequence-Based Amplification (NASBA) method, a Loop-Mediated Isothermal Amplification (LAMP) method, and a rolling circle amplification (RCA) reaction. Further, the nucleic acid probe to be used can be appropriately designed according to the amplification reaction to be employed by those skilled in the art.

Alternatively, in the case where a transcription factor promoter sequence is contained in the nucleic acid probe described above, in the nucleic acid amplification step, a transcription reaction from cDNA to cRNA using the transcription factor may be performed. Examples of such a transcription factor include, as described above, T7 RNA polymerase, SP6 RNA polymerase, and T3 RNA polymerase. After transcription to cRNA is performed, complementary strand synthesis of cDNA and a nucleic acid amplification reaction can be performed again.

After the nucleic acid amplification step, by using the obtained amplification product, gene expression can be analyzed by any method known in the art. For example, in an embodiment, by sequencing the amplification product, the presence or absence of expression of a gene to be analyzed, a position or a region where the gene is expressed (based on the cell recognition tag sequence), the expression level of the gene (corrected based on the molecule recognition tag sequence), or the like can be analyzed. Further, in another embodiment, by using a labeled nucleic acid probe having a complementary sequence to the above-mentioned gene-specific sequence, the labeled nucleic acid probe is hybridized to the cDNA strand constituting the cDNA library or the obtained amplification product, and the expression of the gene to be analyzed can be detected (for example, detected optically) based on the label. The nucleic acid probe to be used in such detection can be appropriately designed by those skilled in the art. Also as the label to be used, any label known in the art can be used, and examples thereof include fluorescent labels (Cy3, fluorescein isothiocyanate (FITC), tetramethylrhodamine isothiocyanate (TRITC), and the like), chemiluminescent labels (luciferin and the like), enzyme labels (peroxidase, β-galactosidase, alkaline phosphatase, and the like), and radioactive labels (tritium, iodine$^{125}$, and the like). In still another embodiment, a nucleic acid amplification reaction is performed using the nucleic acid probe having a complementary sequence to the above-mentioned gene-specific sequence, and the presence or absence of amplification can be detected based on chemiluminescence or fluorescence, whereby the expression of a gene to be analyzed can be analyzed.

In the invention, by associating the analysis results of gene expression in the cDNA library obtained as described above with the two-dimensional positional information of a sample (individual cells, a tissue, or the like), it is also possible to obtain data of correlation between a specific position of individual cells in a tissue and the gene expression level. Examples of such two-dimensional positional information of a sample include a microscopic image of a cell-sample or a tissue section sample, a fluorescence image, and a chemiluminescence image obtained by another labeling method.

In still another embodiment, in the method of the invention, in place of hybridization of the test nucleic acid to the nucleic acid probe as described above, an arbitrary biomolecule is hybridized to a probe molecule containing a sequence for capturing the biomolecule (for example, a ligand capable of specifically binding to the biomolecule, specifically, an antibody, an aptamer, or the like) and a cell recognition tag sequence, the expression of the biomolecule is analyzed on the support to obtain quantitative data, further, a microscopic image is obtained by observation with a microscope before extracting the biomolecule from individual cells, and the microscopic image and the quantitative data of the biomolecule can be associated with each other. Examples of the biomolecule to be analyzed in such a method include any molecules such as proteins, peptide nucleic acids, macromolecules (polymers), and micromolecules. Since the biomolecule is captured on the support by utilizing a specific bond, the biomolecule preferably has a specifically binding ligand. For example, as the biomolecule, a protein is selected, and as the specifically binding ligand (biomolecule capture sequence), an antibody or an aptamer can be selected.

Further, the invention relates to a device and an apparatus for performing the gene expression analysis method as described above.

The device for gene expression analysis according to the invention includes a support in which a nucleic acid probe having a test nucleic acid capture sequence and a known sequence, and further containing a cell recognition tag sequence which differs depending on the difference in position on the surface of the support or in the vicinity of the surface thereof, and a common primer sequence having a known sequence is two-dimensionally distributed and immobilized on the surface of the support or in the vicinity of the surface thereof. The nucleic acid probe may further contain a molecule recognition tag sequence. The nucleic acid probe and the support are as described above.

Further, according to one embodiment, an apparatus for gene expression analysis according to the invention includes:

the device for gene expression analysis described above;

a means for introducing a reagent for synthesizing a complementary DNA strand to the test nucleic acid to serve as a target into the device for gene expression analysis;

a means for introducing a reagent for performing nucleic acid amplification into the device for gene expression analysis; and a means for controlling the temperature of the device for gene expression analysis.

The temperature control means is not particularly limited as long as it is a temperature control means suitable for performing the amplification reaction in the nucleic acid amplification step. Further, the apparatus for gene expression analysis may further include a microscope and a means for associating a microscopic image obtained by observation with the microscope before extracting the test nucleic acid to serve as a target from individual cells with the quantitative data of the test nucleic acid obtained using the device.

According to another embodiment, an apparatus for biomolecule expression analysis according to the invention includes:

a support in which a probe molecule having a biomolecule capture sequence and a known sequence, and further containing a cell recognition tag sequence which differs depending on the difference in position on the surface of the support or in the vicinity of the surface thereof is two-dimensionally distributed and immobilized on the surface of the support or in the vicinity of the surface thereof;

a microscope; and a means for associating a microscopic image obtained by observation with the microscope before extracting the biomolecule from individual cells with the quantitative data of the biomolecule obtained using the support.

In the apparatus for gene expression analysis and the apparatus for biomolecule expression analysis described above, the microscope is not particularly limited as long as a sample such as individual cells (including cells arranged in an array) or a tissue can be observed with the microscope, and for example, a phase-contrast microscope, a fluorescence microscope, a Raman microscope, a differential interference microscope, a laser scanning confocal fluorescence microscope, a nonlinear Raman microscope (a CARS microscope, an SRS microscope, or an RIKE microscope), an IR microscope, or the like can be used.

The apparatus for gene expression analysis and the apparatus for biomolecule expression analysis described above may include a means for capturing cells on the support (for example, a means for arranging cells in an array on the support).

EXAMPLES

Hereinafter, specific examples of embodiments of the invention will be described with reference to drawings. However, it should be noted that these Examples are merely illustrative for embodying the invention and do not limit the invention.

Example 1

This Example is an example of using a two-dimensional cDNA library sheet which was constructed in a pore array sheet (one example of the device for gene expression analysis) from a group of cells in a sheet form while keeping the positional information of mRNA contained therein. Hereinafter, a sheet in which a large number of pores are two-dimensionally formed will be referred to as a pore array sheet, and a pore array sheet in which a cDNA library is formed will be referred to as a cDNA library pore array sheet. A conceptual view of this method, and a configuration example and a use mode of the device for gene expression analysis (a pore array sheet) to be used are shown in FIGS. 1A-1E.

This method includes extracting mRNA while keeping the positional information of cells 2 arranged in a sheet form and capturing mRNA 4 by a DNA probe 6 immobilized on an internal portion of a pore array sheet 1 (FIG. 1A), preparing a cDNA library by reverse transcription (synthesis of a 1st cDNA strand 9) in the internal portion of the sheet 1 (FIG. 1B), subsequently synthesizing a 2nd cDNA strand 21 (FIGS. 1C, 1D), and performing PCR amplification (FIG. 1E).

In order to prepare a cDNA library while keeping the positional information of cells, it is necessary to extract mRNA 4 to immediately below the cells 2 and capture the mRNA 4 in the internal portion of the sheet 1. In order to achieve this, disruption of cells and electrophoresis of nucleic acids (mRNA 4) are simultaneously performed. In order to transfer the positional information of the cell in which the captured mRNA was originally present is transferred to the sequence information, the DNA probe 6 immobilized on the internal portion of the sheet 1 contains a cell recognition tag sequence having a sequence which differs per position or region in the sheet, and mRNA is captured by this DNA probe. The different patterns 3 on the pore array sheet 1 in FIG. 1A show that the DNA probe 6 having a different cell recognition tag sequence is immobilized. This DNA probe 6 for capturing mRNA includes, from the 5'-terminal side, a common sequence for PCR amplification (Forward direction), a cell recognition tag sequence, a molecule recognition tag sequence, and an oligo(dT) sequence. By introducing the common sequence for PCR amplification into the DNA probe, in the subsequent PCR amplification step, this sequence can be used as a common primer. Further, by introducing the cell recognition tag sequence (for examples, 5 bases) into the DNA probe, $4^5=1024$ positions or regions (for example, $4^5=1024$ single cells) can be recognized. That is, a cDNA library can be prepared from 1024 single cells at a time, and therefore, an effect that the cost of reagents and the labor can be reduced to $1/1024$ is obtained, and also it becomes possible to identify as to which cell or position or region the sequence data finally obtained with a next generation sequencer is derived from. Further, by introducing the molecule recognition tag sequence (for examples, 15 bases) into the DNA probe, $4^{15}=1.1\times10^9$ test molecules (here, mRNA) can be discriminated, and therefore, it is possible to identify as to which molecule the enormous decoded data obtained with a next generation sequencer is derived from. That is, in the amplification step, amplification efficiency bias occurs depending on the sequence or the length of DNA, the volume for performing the amplification reaction, or the like, however, by utilizing the molecule recognition tag sequence, the amplification bias among genes occurring in the amplification step can be corrected, and therefore, it becomes possible to quantitatively determine the level of mRNA originally present in the sample with high accuracy. The oligo(dT) sequence located at the most 3'-terminal side is a test nucleic acid capture sequence and is hybridized to the poly A tail added to the 3'-terminal side of the mRNA, and therefore, utilized for capturing the mRNA (FIG. 1A). Here, as the DNA probe 6, a 30-base common sequence for PCR amplification (Forward direction), a 5-base cell recognition tag sequence, a 15-base molecule recognition tag sequence composed of a random sequence, and an 18-base oligo(dT) sequence attached with a 2-base VN sequence (SEQ ID NO: 1) were included.

In this embodiment, in order to analyze mRNA, a poly T sequence was used as part of the capture DNA probe, however, when microRNA or a genome is analyzed, in place of the poly T sequence, a random sequence or part of a complementary sequence to the sequence to be analyzed may be used.

Next, a method for preparing the cDNA library sheet will be described in detail. As the pore array sheet for preparing the cDNA library, any of various materials such as a monolith sheet formed of porous glass, a capillary plate prepared by bundling capillaries, followed by slicing, a nylon membrane, or a gel thin film can be used. However, here, a porous array sheet obtained by anodizing alumina was used. Such a sheet can also be prepared by anodization by oneself, however, a porous sheet having a pore diameter of 20 nm to 200 nm can be obtained as a commercially available product. Here, an example in which the pore array sheet 1 having a pore diameter of 200 nm, a thickness of 60 μm, and a diameter of 25 mm is used will be described, however, the shape of the pore array sheet is not limited thereto. The pore 5 formed in the sheet 1 goes through the sheet 1 in the thickness direction of the sheet 1, and the pores are completely mutually independent. The surface is hydrophilic, and adsorption of proteins on the surface is extremely low, and thus, an enzymatic reaction efficiently proceeds. First, the surface of the pore array sheet 1 is treated with a silane coupling agent, and the DNA probes 6 are immobilized on the pore surfaces. Since the DNA probes 6 are immobilized on the surface at a ratio of one per 30 to 100 nm$^2$ in average, 4 to $10 \times 10^6$ DNA probes are immobilized per pore. Subsequently, in order to prevent surface adsorption, the surface is coated with a surface coating agent. The surface coating may be performed simultaneously with immobilization of the probes. This DNA probe density is a density capable of capturing mRNA passing through this space on the DNA probe at an efficiency of almost 100%.

Next, a method in which mRNA is extracted from a group of cells and a cDNA library is prepared in a pore array sheet will be described. A gel containing a cell-lysis reagent 7 (for example, a mixed liquid of a surfactant and an enzyme) for disrupting the cell membrane is placed on the upper portion of the pore array sheet 1 as shown in FIG. 1A. Here, reference numeral 2 denotes a group of cells of a sample and reference numeral 7 denotes the gel containing the cell lysis reagent. Then, the upper portion on which the cell sample in a sheet form is placed is brought into contact with a solution containing an electrolyte. Needless to say, the cells may be in direct contact with the electrolyte, or may be brought into contact with the electrolyte through the gel or the like. On the other hand, a gel 8 in the lower portion is also brought into contact with the solution containing an electrolyte passing through the pores so that an electric field is applied in the vertical direction of the cell sheet 1. Negatively charged mRNA 4 is electrophoretically moved to the lower portion through the pore 5, and the poly A tail of the mRNA 4 is captured by the oligo(dT) sequence of the DNA probe 6 in the pore 5. As shown on the right side of FIG. 1A, after mRNA 4 is captured in the pore 5, the sample and the gel sheet 7 are removed, however, it is advantageous to use a low melting-point agarose gel which is a gel causing a phase conversion depending on temperature as a gel material. That is, the agarose gel turns into a liquid by increasing the temperature, and therefore can be washed off.

Subsequently, a 1st cDNA strand 9 is synthesized using the mRNA 4 captured by the DNA probe 6 in the pore 5 as a template. In this step, the pore 5 is filled with a solution containing a reverse transcriptase and a synthetic substrate, and a complementary strand synthesis reaction is performed for about 50 minutes by gradually increasing the temperature to 50° C. (FIG. 1B). After completion of the reaction, RNase is allowed to flow through the pore 5 to degrade and remove the mRNA 4. Then, a liquid containing an alkaline denaturant and a washing liquid are passed through the pore 5 to remove the residue and the degraded products. By the above procedures, a cDNA library sheet as shown in FIG. 1B reflecting the position of individual cells in a tissue is constructed in the pore 5.

Subsequently, plural types (up to 100 types) of target gene-specific sequence primers 20 added with a common sequence for PCR amplification (Reverse) are annealed to the 1st cDNA strand 9 (FIG. 1C), and by a complementary strand elongation reaction, a 2nd cDNA strand 21 is synthesized (FIG. 1D). That is, the 2nd cDNA strand is synthesized under multiplex conditions. By doing this, with respect to the multiple target genes, a double-stranded cDNA 22 having the common sequences for PCR amplification (Forward/Reverse) at both ends, and containing the cell recognition tag sequence, the molecule recognition tag sequence, and the gene-specific sequence is synthesized. Further, in this embodiment, as one example, with respect to 20 types (ATP5B, GAPDH, GUSB, HMBS, HPRT1, RPL4, RPLP1, RPS18, RPL13A, RPS20, ALDOA, B2M, EEF1G, SDHA, TBP, VIM, RPLP0, RPLP2, RPLP27, and OAZ1) of target genes, sequences composed of 20±5 bases in a region 109 ±8-bases upstream from the poly A tail of each of the target genes were used as the gene-specific sequences (represented by SEQ ID NOS: 3 to 22, respectively). This is because the PCR products are made to have the same size of about 200 bases in the subsequence PCR amplification step. By making the PCR products have the same size, an effect that a complicated size fractionation purification step (electrophoresis→cutting out of gel→extraction and purification of PCR products) can be avoided, and the PCR products can be directly used for parallel amplification (emulsion PCR or the like) from one molecule is obtained. Subsequently, PCR amplification is performed by utilizing the common sequences for PCR amplification (Forward/Reverse), whereby PCR products derived from plural types of genes are prepared (FIG. 1E). In this step, even if amplification bias occurs among genes or molecules, after next generation sequencer data are obtained, the amplification bias can be corrected by utilizing the molecule recognition tag sequence, and therefore, highly accurate quantitative data can be obtained.

The number of mRNAs per cell is approximately $10^6$. Assuming that a cell is schematically a round cell having a size of 10 μm in diameter, the number of pores to be used per cell may come to about 2500. That is, if the number of mRNAs expressed in a single cell is 1000 copies or less, one copy of cDNA can be produced per pore in average. If the number of mRNAs is larger than 1000, multiple copies of cDNA for the same type of mRNA are produced per pore. It is also possible to decrease the number of copies for each type of mRNA per pore to 1 or less by decreasing the size of the pore. (Further, it is also possible to decrease the number of copies per cell to 1 or less by treating cells one by one to increase the region for preparing the cDNA library per cell). In each pore, various types of 400 cDNAs are produced in average. Here, a case where the 2nd cDNA strand is synthesized from the thus produced cDNA (1st cDNA strand) using several tens of types of gene-specific sequence primers added with the common sequence for PCR amplification, and an example which PCR amplification is performed is disclosed. Needless to say, other amplification methods such as rolling circle amplification (RCA), NASBA, and LAMP methods may be used.

Next, a method for immobilizing the DNA probe on the internal portion of the pore of the cDNA library sheet will be described in detail. The surface of the pore in the internal portion of the sheet needs to be a surface on which the DNA probe is immobilized at high density and at the same time, nucleic acids such as mRNA and primers for PCR amplification, and proteins such as a reverse transcriptase and a polymerase are not adsorbed. In this Example, a silane coupling agent for immobilizing the DNA probe and a silanated MPC polymer for preventing adsorption were simultaneously immobilized in an appropriate ratio on the surface of the pore via a covalent bond, thereby realizing highly dense immobilization of DNA and stable prevention of adsorption of nucleic acids and proteins. Actually, first, a porous sheet 1 made of alumina was immersed in an ethanol solution for 3 minutes. Then, a UVO3 treatment is performed for 5 minutes, followed by washing three times with ultrapure water. Subsequently, the sheet was immersed in a 80% ethanol solution containing 3 mg/ml of $MPC_{0-8}$-

MPTMSi$_{0.2}$ (MPC: 2-Methacryloyloxyethyl phosphorylcholine, MPTMSi: 3-Methacryloxypropyl trimethoxysilane) (see, Biomaterials 2009, 30: 4930-4938, and Lab Chip 2007, 7, 199-206) serving as a silanated MPC polymer having an average molecular weight of 9700 (polymerization degree: 40), 0.3 mg/ml of a silane coupling agent GTMSi (GTMSi: 3-Glycidoxypropyltrimethoxysilane, Shin-Etsu Chemical Co., Ltd.), and 0.02% acetic acid serving as an acid catalyst for 2 hours. After washing the sheet with ethanol, the sheet was dried in a nitrogen atmosphere and heated in an oven at 120° C. for 30 minutes. Subsequently, 0.05 M borate buffer (pH 8.5) containing 1 μM of the DNA probe (SEQ ID NO: 1) modified with an amino group at the 5' end, 7.5% glycerol, and 0.15 M NaCl was ejected onto the sheet by the same technique as the inkjet printer so that the DNA probe containing the cell recognition tag sequence (1024 types) which differs per region (25 μm×25 μm) was ejected at 100 pL/region. Thereafter, a reaction was performed at 25° C. for 2 hours in a humidified chamber. At the end, in order to block unreacted glycide groups and remove excess DNA probes, the sheet was washed with a sufficient amount of a borate buffer (pH 8.5) containing 10 mM Lys, 0.01% SDS, and 0.15 M NaCl for 5 minutes. After this washing liquid was removed, the sheet was washed with 30 mM sodium citrate buffer containing 0.01% SDS and 0.3 M NaCl (2×SSC, pH 7.0) at 60° C. to remove excess DNA. In this manner, immobilization of the DNA probe and the surface treatment were completed.

Figure 2:
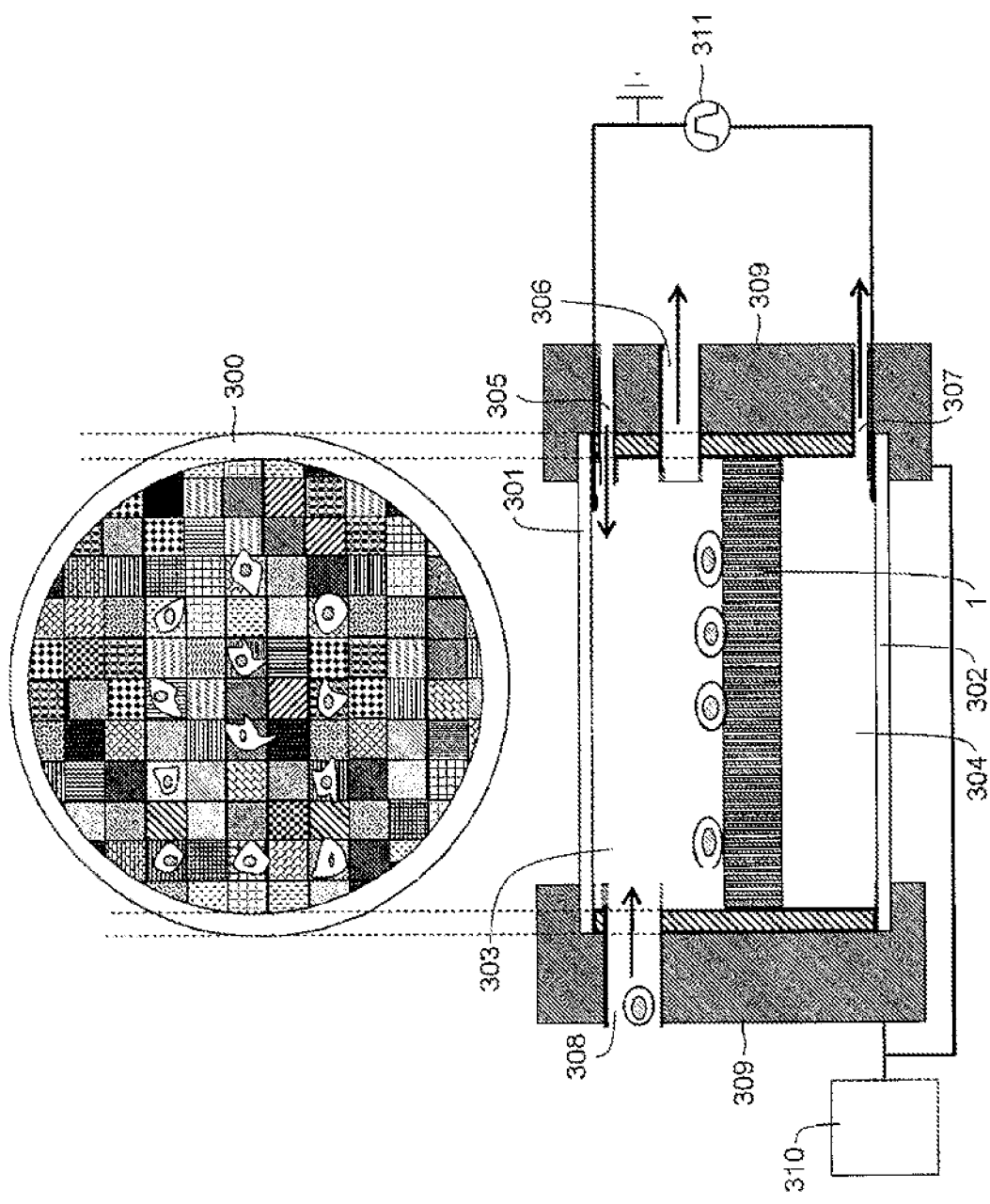
FIG. 2 is a view showing an upper surface and a cross section of one example of a reaction cell for capturing cells.

Hereinafter, an apparatus system for preparing a cDNA library sheet from a cell array and obtaining a gene expression profile with a next generation (large-scale) sequencer described above will be explained. A cell array will be described as an example, however, the same is applied to the case where a tissue section is used. After cells (about 1000 cells or less) are washed with 500 μL of 1×PBS so as not to damage the cells, the solution was removed so as to leave no PBS as much as possible. Then, 50 μL of 1×PBS cooled to 4° C. was added thereto. This sample is arranged in an array on a sheet 1. Specifically, on a sheet having 0.1-μm pores and a thickness of 60 μm, positively charged regions having a diameter of 20 μm are provided at intervals of 25 μm by a surface treatment. Since the surfaces of the cells are negatively charged, when the cells are allowed to flow on the surface of the sheet, the cells are captured on the surface at intervals of 25 μm. That is, in a region where one cell is captured, 4 types of cell recognition tag sequences are immobilized. Actually, when cells were allowed to flow and captured, the cells could be captured one by one at about 20% of the positions FIG. 2 shows an example of a reaction cell used for capturing cells (that is, for preparing a cell array). By using the reaction cell, cells 2 can be immobilized one by one on the sheet 1 having a diameter of 25 mm and the internal portions of the pores can be filled with a solution. A protection ring 300 made of polypropylene is provided in a peripheral portion of the sheet 1 so that the surroundings of the sheet are filled with a solution, and sandwiched by an upper cover 301 and a lower cover 302, located above and below the sheet 1, respectively, and each having a transparent (ITO) electrode formed by sputtering on the inner side thereof, whereby an upper reaction region 303 and a lower reaction region 304 for being filled with a reaction solution are formed. The reason why the electrode is made transparent is because the cells can be observed with an optical microscope, and the ITO transparent electrode used here has a transmittance of 40% or more in the wavelength range of 400 to 900 nm. A buffer solution was injected from an inlet 305 and discharged from an upper outlet 306 and a lower outlet 307, whereby the internal portion was filled with the solution. Subsequently, a group of cells were allowed to flow in the reaction cell from a cell channel (inlet 308) while shaking the reaction cell. The cells are captured in a positively charged portion, however, needless to say, the cells may be captured using a container or a compartment in which one cell is housed. Subsequently, by using a solution obtained by mixing a cell-lysis reagent with a low melting-point agarose gel (SeaPrep Agarose; gelation temperature: 19° C., melting point: 45° C. at a concentration of 2%) which causes phase conversion between a gel state and a liquid state depending on temperature, a cell membrane and a cell tissue are disrupted and mRNA is extracted while fixing the positions of the cells on the sheet.

A 4% SeaPrep Agarose (Cambrex Bio Science Rockland, Inc.) solution (250 μL), a Lysis Solution (495 μL) (TaqMan MicroRNACell-to-CT Kit; Applied Biosystems, Inc.), and DNase I (5 μL) were mixed well at 40° C. Subsequently, the temperature of the sheet 1 is set to 4° C. After the solution is removed from the reaction regions 303 and 304, the above-mentioned cell lysis reagent solution is injected through the inlet 305. After confirming that the solution on the sheet was gelatinized, the temperature of the sheet was increased to 20° C., and a reaction was performed for 8 minutes. Thereafter, 50 μL of a Stopping Solution (a solution for inactivating DNase) was added onto the gel and reacted for 5 minutes, and then, the gel was cooled to 4° C. Subsequently, 0.5 mL of 10 mM Tris buffer (pH 8.0) containing 0.03% PEO (polyethylene oxide) having a molecular weight of 600,000, 0.03% PVP (polyvinylpyrrolidone) having a molecular weight of 1,000,000, and 0.1% Tween 20 was added thereto. At this time, the distance between the upper electrode 301 and the lower electrode 302 is set to 2 mm and the spaces (reaction regions 303 and 304) above and below the sheet are completely filled with the above-mentioned Tris buffer. While maintaining the temperature of the sheet and the solution at 4° C., a voltage of +5 V is applied for 2 minutes with a power source 311 by using the upper electrode 301 as a cathode (GND) and the lower electrode 302 as an anode, and negatively charged mRNA is electrophoresed from the inside of the cells toward the reaction region 304 (electrophoresis conditions: pulse electrophoresis (on level: 10 V, off level: 0 V, frequency: 100 kHz, duty: 50%) may be employed in place of application of DC voltage).

In this process, most mRNAs are trapped by the oligo (dT) portions of the DNA probes immobilized on the pores in the sheet (FIG. 1A). However, some mRNAs are not trapped by the two-dimensional structure and moves into the buffer (304) below the sheet. In order to trap mRNAs completely by the DNA probes, the temperature of the sheet 1 and the solution was increased to 70° C. and maintained for 5 minutes, and thereafter cooled to 4° C. at –0.1° C./sec while reversing the polarity of the voltage applied to the lower electrode 302 at every one minute (in the beginning, a voltage of –5 V was applied for one minute, and thereafter, voltages of +5 V and –5 V were alternately applied for one minute each. This operation was repeated 10 times). Subsequently, while exchanging the solution in the region 303 above the sheet 1 by introducing the above-mentioned Tris buffer from the inlet 305 and discharging it from the outlet 306, the temperature of the solution and the sheet 1 was increased to 35° C. to melt the agarose gel and unnecessary cell tissues and agarose were washed off. Further, 585 μL of 10 mM Tris buffer (pH 8.0) containing 0.1% Tween 20, 40 μL of 10 mM dNTP, 225 μL of 5×RT buffer (SuperScript III, Invitrogen Corporation), 40 µL of 0.1 M DTT, 40 µL of RNaseOUT (Invitrogen Corporation), and 40 µL of Superscript III (reverse transcriptase, Invitrogen Corporation) were mixed. The solution soaking the sheet 1 was discharged from the outlets 306 and 307, and immediately thereafter, the solution containing the reverse transcriptase prepared above was injected from the inlet 305. Thereafter, the temperature of the solution and the sheet 1 was increased to 50° C. and maintained for 50 minutes to complete the reverse transcription reaction, whereby a 1st cDNA strand having a complementary sequence to the mRNA was synthesized (FIG. 1B).

Here, cDNA is prepared by using about 10,000 pores per cell. The total surface area of the pores per cell is about 0.7 mm$^2$. Since one or more DNA probes are immobilized per 100 nm$^2$, the total number of probes is about $7 \times 10^9$. This is a sufficient amount for capturing mRNAs (total number: about $10^6$) in one cell. Since the nucleic acids are easily adsorbed on the surface in the pore, the surface of the pore is coated with an MPC polymer as a surface coating agent to prevent adsorption as described above.

By the operation described above, cDNAs immobilized on the surfaces of a large number of pores for each cell were obtained in the form of a library. This should be referred to as a so-called single-cell cDNA library sheet and is fundamentally different from a conventional averaged cDNA library obtained from a large number of cells.

From the thus obtained cDNA library sheet, the expression level of each gene is quantitatively measured for various genes. Since there are 10,000 pores per cell, the number of cDNAs per pore is 100 in average. With respect to one type of cDNA, if the number of copies of cDNA per cell is 10,000 or less, an average number of copies of cDNA per pore is one or less.

After the 1st cDNA strand was synthesized, the reverse transcriptase was inactivated by maintaining the temperature at 85° C. for 1.5 minutes, followed by cooling to 4° C. Thereafter, 10 mL of 10 mM Tris buffer (pH 8.0) containing RNase and 0.1% Tween 20 was injected from the inlet 305 and discharged from the outlets 306 and 307, thereby degrading RNA, and then, the same amount of an alkaline denaturant was allowed to flow therein in the same manner, thereby removing and washing the residue and the degraded products in the pores. Subsequently, 690 µL of sterile water, 100 µL of 10× Ex Taq Buffer (TaKaRa Bio, Inc.), 100 µL of 2.5 mM dNTP Mix, 100 µL of a primer mix of 20 types of gene-specific sequences (SEQ ID NOS: 3 to 22, 10 µM each) added with a common sequence for PCR amplification (Reverse, SEQ ID NO: 2), and 10 µL of Ex Taq Hot start version (TaKaRa Bio, Inc.) were mixed. The solution soaking the sheet was discharged from the outlets 306 and 307, and immediately thereafter, the solution containing the reverse transcriptase prepared above was injected from the inlet 305. Thereafter, the solution and the sheet were subjected to a reaction under the following conditions: 95° C. for 3 minutes →44° C. for 2 minutes →72° C. for 6 minutes, whereby the gene-specific sequence of the primer 20 was annealed by using the 1st cDNA strand 9 as a template (FIG. 1C). Thereafter, a complementary strand elongation reaction was performed, whereby a 2nd cDNA strand 21 was synthesized (FIG. 1D).

Subsequently, 495 µL of sterile water, 100 µL of 10× High Fidelity PCR Buffer (Invitrogen Corporation), 100 µL of 2.5 mM dNTP mix, 40 µL of 50 mM MgSO$_4$, 100 µL of 10 µM common sequence primer for PCR amplification (Forward, SEQ ID NO: 23), 100 µL of 10 µM common sequence primer for PCR amplification (Reverse, SEQ ID NO: 2), and 15 µL of Platinum Taq Polymerase High Fidelity (Invitrogen Corporation) were mixed. The solution soaking the sheet was discharged from the outlets 306 and 307, and immediately thereafter, the solution prepared above was injected from the inlet 305. Thereafter, the solution and the sheet were maintained at 94° C. for 30 seconds and subjected to the following 3-step cycle: 94° C. for 30 seconds→55° C. for 30 seconds→68° C. for 30 seconds. The cycle was repeated 40 times. After the solution and the sheet were maintained at 68° C. for 3 minutes at the end, the temperature was decreased to 4° C., and the PCR amplification step was performed (FIG. 1E). In order to realize such a thermal cycle, a configuration in which a heat block 309 (an aluminum alloy or a copper alloy) with a heater and a temperature controller 310 are provided was adopted. According to this, a region of interest of each of the 20 types of target genes is amplified, however, all PCR products have substantially the same size of 200±8 bases. The PCR amplification product solution accumulated in the pores of the sheet and in the external solution is collected. Purification is performed using PCR Purification Kit (QIAGEN, Inc.) for the purpose of removing free common sequence primers for PCR amplification (Forward/Reverse) and residual reagents such as enzymes contained in this solution. After this solution is subjected to emPCR amplification or bridge amplification, sequence analysis is performed by subjecting the amplification product to any of next generation sequencers of different companies (for example, Life Technologies (Solid/Ion Torrent), Illumina (High Seq), and Roche 454).

Figure 3:
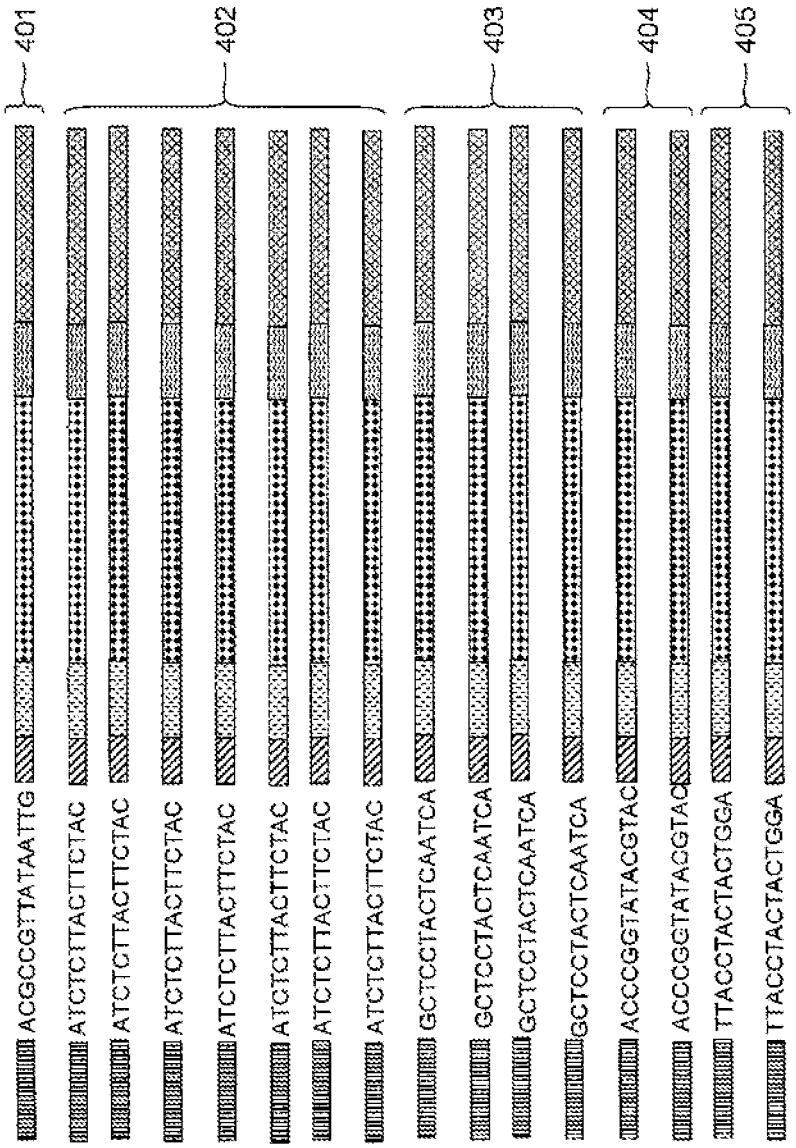
FIG. 3 is a view schematically showing sequencing data of PCR amplification products containing a molecule recognition tag sequence.

Next, a method for reducing amplification bias using the molecule recognition tag sequence will be described. In FIG. 3, a state where sequencing data are obtained as the same sequences other than the molecule recognition tag sequence is schematically shown (Relevant portions of the obtained sequencing data are schematically shown). In FIG. 3, reference numerals 401, 402, 403, 404, and 405 denote the same sequences inclusive of the molecule recognition tag sequence which is a random sequence, and cases where 1, 7, 4, 2, and 2 reads (apparent molecule count) are obtained, respectively, are shown. In FIG. 3, reference numeral 401 includes SEQ ID NO. 25, reference numeral 402 includes SEQ ID NO. 26, reference numeral 403 includes SEQ ID NO. 27, reference numeral 404 includes SEQ ID NO. 28, reference numeral 405 includes SEQ ID NO. 29. These sequences are all one molecule when the 2nd cDNA strand was synthesized in FIG. 1D, and the number of molecules is increased by the PCR amplification thereafter, and at the same time, the number of molecules becomes different. Therefore, the reads having the same molecule recognition tag sequence may be regarded as the same molecule, and all are regarded as one molecule. As a result, bias of the number of molecules for each sequence due to PCR amplification in the step after synthesizing the 2nd cDNA strand or adsorption on the inner portion of the pore array sheet when the solution is taken out to the outside is eliminated by utilizing the molecule recognition tag sequence.

The sheet prepared here can be used repeatedly, and with respect to a group of genes whose expression level is required to be known, a solution of gene-specific sequence primer mix added with a common sequence primer for PCR amplification (Reverse, SEQ ID NO: 2) is prepared, and in the same manner as described above, synthesis of the 2nd cDNA strand, PCR amplification, and emPCR are performed, and then, analysis may be performed with a next generation sequencer. That is, by repeatedly using the cDNA library, highly accurate expression distribution measurement can be performed for necessary types of genes.

Alternatively, the amplification step may be performed in a liquid phase by collecting the cDNA library (cDNA strand) from the cDNA library pore array sheet.

Example 2

This Example is an example of using a two-dimensional cDNA library sheet which was constructed in a pore array sheet from a group of cells in a sheet form while keeping the positional information of mRNA contained therein, and is an example of a case where a transcription factor T7 promoter was used in place of PCR amplification.

Figures 4A, 4B:
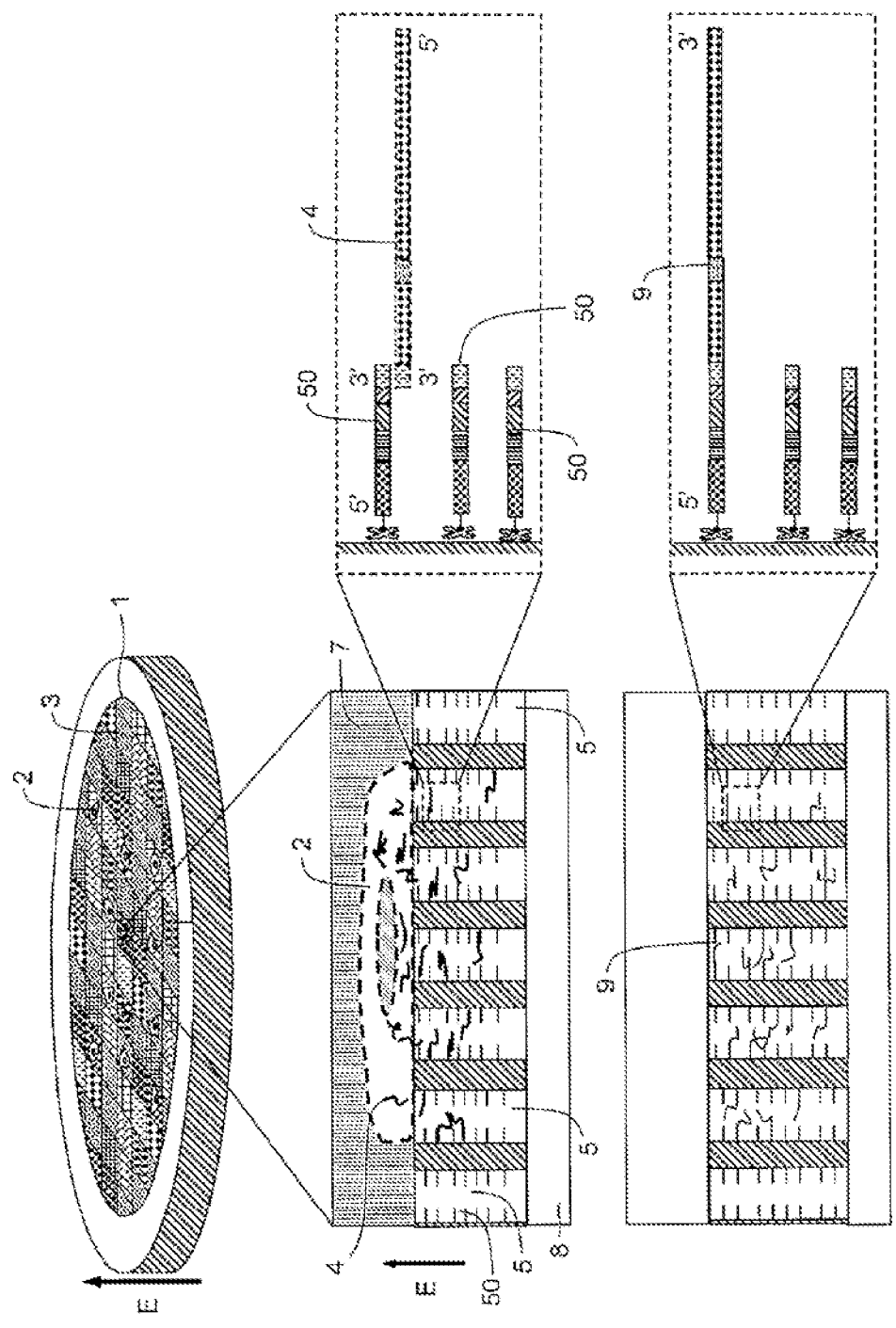
FIGS. 4A and 4B are views showing another example of the method of the invention and a configuration example and a use mode of a device for gene expression analysis (a pore array sheet) to be used.

The points of change from Example 1 in the method of this Example are shown in FIGS. 4A-4H. A DNA probe 50 (SEQ ID NO: 24) immobilized on an internal portion of a sheet includes, from the 5'-terminal side, a T7 promoter sequence (base numbers 1 to 42), a common sequence for amplification (Forward direction) (base numbers 43 to 72), a cell recognition tag sequence (base numbers 73 to 77), a molecule recognition tag sequence (base numbers 78 to 92), and an oligo(dT) sequence (added with a VN sequence) (base numbers 93 to 102). By introducing the T7 promoter sequence into the DNA probe, a target sequence can be amplified in the amplification step (FIG. 4E) of cRNA 63 by the subsequent IVT (In Vitro Transcription). That is, the T7 promoter sequence is recognized by T7 RNA polymerase, and a reaction of transcription (amplification of cRNA 63) of a sequence downstream of the T7 promoter sequence is started. In the same manner, by introducing the common sequence for amplification, it can be used as a common primer in the subsequent emPCR amplification step. Further, by introducing the cell recognition tag sequence (for example, 5 bases) into the DNA probe, $4^5$ (=1024) regions or positions (that is, $4^5$=1024 single cells) can be recognized, which is the same as in Example 1. Further, by introducing the molecule recognition tag sequence (for examples, 15 bases) into the DNA probe, $4^{15}$ (=1.1×10$^9$) molecules can be discriminated, and therefore, it is possible to identify as to which molecule the enormous decoded data obtained with a next generation sequencer is derived from, which is also the same as in Example 1. That is, amplification bias among genes occurring in the amplification step such as IVT/emPCR can be corrected, and therefore, it becomes possible to quantitatively determine the level of mRNA originally present in the sample with high accuracy. The oligo(dT) sequence located at the most 3'-terminal side is hybridized to the poly A tail added to the 3'-terminal side of the mRNA, and therefore, utilized for capturing the mRNA (FIG. 4A).

Figures 4C, 4D, 4E:
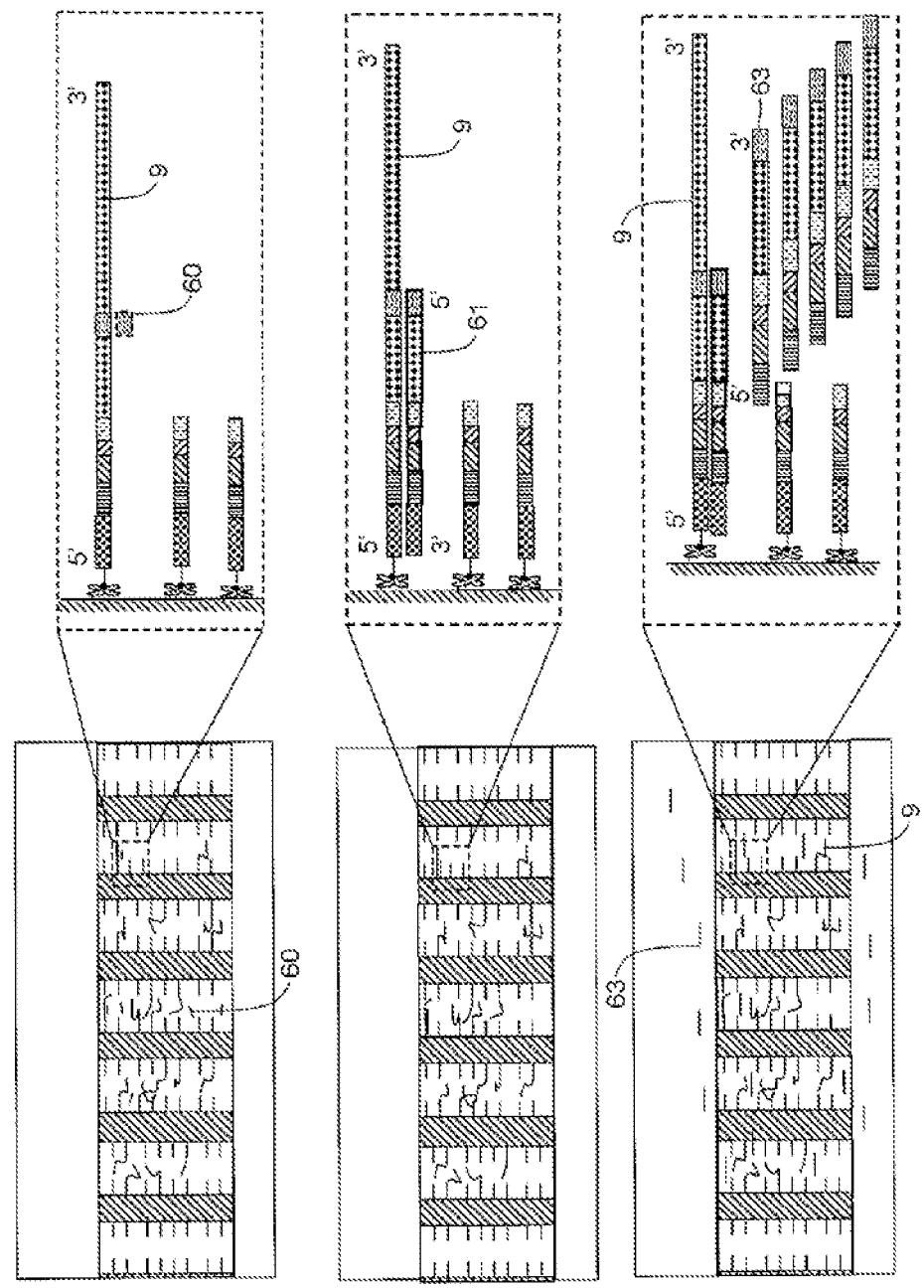
FIGS. 4C-4E are views showing another example of the method of the invention and a configuration example and a use mode of a device for gene expression analysis (a pore array sheet) to be used.

Next, the respective steps of the reaction will be sequentially described. As shown in FIG. 4A, mRNA 4 is captured by an 18-base poly T sequence which is a complementary sequence to the poly A sequence at the 3' end of the mRNA 4 in the same manner as in Example 1. Subsequently, a 1st cDNA strand 9 is synthesized, whereby a cDNA library is constructed (FIG. 4B). Subsequently, any of plural types (up to 100 types) of target gene-specific sequence primers 60 corresponding to the genes to be quantitatively determined was annealed to the 1st cDNA strand 9 (FIG. 4C), and by a complementary strand elongation reaction, a 2nd cDNA strand 61 is synthesized (FIG. 4D). That is, the 2nd cDNA strand is synthesized under multiplex conditions. By doing this, with respect to the multiple target genes, double-stranded cDNAs having the common sequences for amplification (Forward/Reverse) at both ends, and containing the cell recognition tag sequence, the molecule recognition tag sequence, and the gene-specific sequence are synthesized. Further, in this embodiment, as an example, with respect to 20 types (ATP5B, GAPDH, GUSB, HMBS, HPRT1, RPL4, RPLP1, RPS18, RPL13A, RPS20, ALDOA, B2M, EEF1G, SDHA, TBP, VIM, RPLP0, RPLP2, RPLP27, and OAZ1) of genes, sequences composed of 20±5 bases in a region 109 ±8-bases upstream from the poly A tail of each of the target genes were used as the gene-specific sequences (represented by SEQ ID NOS: 3 to 22, respectively). This is because the amplification products are made to have the same size of about 200 bases in the subsequence IVT amplification step. By making the amplification products have the same size, a complicated size fractionation purification step (electrophoresis →cutting out of gel→extraction and purification of amplification products) can be avoided, and the amplification products can be directly used for parallel amplification (emulsion PCR or the like) from one molecule. Subsequently, T7 RNA polymerase is introduced into the pores, and cRNA 63 is synthesized (FIG. 4E). In this step, about 1000 copies of cRNA 63 are synthesized. Further, in order to synthesize a double-stranded DNA for emPCR, by using the amplified cRNA 63 as a template, plural types (up to 100 types) of target gene-specific sequence primers 71 added with a common sequence for PCR amplification (Reverse) are hybridized (FIG. 4F), whereby cDNA 72 is synthesized (FIG. 4G). Further, in the same manner as in Example 1, after the cRNA is degraded using an enzyme, a 2nd cDNA strand is synthesized using a common primer for PCR amplification (Forward), whereby a double-stranded DNA 73 for emPCR is synthesized (FIG. 4H). The obtained amplification products have the same size, and therefore can be directly applied to emPCR and a next generation sequencer. In this step, even if amplification bias occurs among genes or molecules, after next generation sequencer data are obtained, the amplification bias can be corrected by utilizing the molecule recognition tag sequence, and therefore, highly accurate quantitative data can be obtained, which is the same as in Example 1 (FIG. 3).

Next, a series of steps will be specifically described. After the 1st cDNA strand was synthesized, the reverse transcriptase was inactivated by maintaining the temperature at 85° C. for 1.5 minutes, followed by cooling to 4° C. Thereafter, 10 mL of 10 mM Tris buffer (pH 8.0) containing RNase and 0.1% Tween 20 was injected from the inlet 305 and discharged from the outlets 306 and 307, thereby degrading RNA, and then, the same amount of an alkaline denaturant was allowed to flow therein in the same manner, thereby removing and washing the residue and the degraded products in the pores. Subsequently, 690 μL of sterile water, 100 μL of 10×Ex Taq Buffer (TaKaRa Bio, Inc.), 100 μL of 2.5 mM dNTP Mix, 100 μL of a primer mix of 20 types of gene-specific sequences (SEQ ID NOS: 3 to 22, 10 μM each) added with a common sequence for PCR amplification (Reverse, SEQ ID NO: 2), and 10 μL of Ex Taq Hot start version (TaKaRa Bio, Inc.) were mixed. The solution soaking the sheet was discharged from the outlets 306 and 307, and immediately thereafter, the solution containing the reverse transcriptase prepared above was injected from the inlet 305. Thereafter, the solution and the sheet were subjected to a reaction under the following conditions: 95° C. for 3 minutes →44° C. for 2 minutes →72° C. for 6 minutes, whereby the gene-specific sequence of the primer was annealed by using the 1st DNA strand as a template (FIG. 4C). Thereafter, a complementary strand elongation reaction was performed, whereby a 2nd cDNA strand was synthesized (FIG. 4D).

Subsequently, 10 mL of 10 mM Tris buffer (pH 8.0) containing 0.1% Tween 20 was injected from the inlet 305 and discharged from the outlets 306 and 307, thereby removing and washing the residue and the degraded products in the pores. Further, 340 μL of sterile water, 100 μL of AmpliScribe 10× Reaction Buffer (EPICENTRE, Inc.), 90 μL of 100 mM dATP, 90 μL of 100 mM dCTP, 90 μL of 100 mM dGTP, 90 μL of 100 mM dUTP, 100 mM DTT, and 100 μL of AmpliScribe T7 Enzyme Solution (EPICENTRE, Inc.) were mixed. The solution soaking the sheet was discharged from the outlets 306 and 307, and immediately thereafter, the solution containing the reverse transcriptase prepared above was injected from the inlet 305. Thereafter, the temperature of the solution and the sheet was increased to 37° C. and maintained for 180 minutes to complete a reverse transcription reaction, whereby cRNA was amplified (FIG. 4C). According to this, a region of interest of each of the 20 types of target genes is amplified, however, all cRNA amplification products have substantially the same size of 200±8 bases. The cRNA amplification product solution accumulated in the pores of the sheet and in the external solution is collected. Purification is performed using PCR Purification Kit (QIAGEN, Inc.) for the purpose of removing residual reagents such as enzymes contained in this solution, and the purified product is suspended in 50 μL of sterile water. In this solution, 10 μL of 10 mM dNTP mix and 30 μL of 50 ng/μL random primers are mixed. The resulting mixture is heated to 94° C. for 10 seconds, and the temperature of the mixture is decreased to 30° C. at 0.2° C./sec and the mixture is heated to 30° C. for 5 minutes, and then the temperature of the mixture is further decreased to 4° C. Thereafter, 20 μL of 5×RT buffer (Invitrogen Corporation), 5 μL of 0.1 M DTT, 5 μL of RNaseOUT, and 5 μL of SuperScript III are mixed, and the resulting mixture is heated to 30° C. for 5 minutes, and the temperature of the mixture is increased to 40° C. at 0.2° C./sec. Purification is performed using PCR Purification Kit (QIAGEN, Inc.) for the purpose of removing residual reagents such as enzymes contained in this solution. After this purified solution is subjected to emPCR amplification, sequence analysis is performed by subjecting the amplification product to any of next generation sequencers of different companies (for example, Life Technologies, Illumina, and Roche).

Example 3

This Example is an example of constructing a cDNA library sheet using a pore array sheet by preparing a cell array of blood cells having low adhesiveness and performing gene expression analysis. In Example 1, in order to prepare a cell array, a surface treatment of a cell array sheet was employed. Therefore, cells were required to have a certain level of adhesiveness. In this Example, an example of an apparatus having a device structure configured to arrange cells in an array by the flow of a solution without resort to the adhesiveness of cells will be described.

FIG. 5A shows a cross-sectional view of a cell array device. In this Example, the measurement target is determined to be white blood cells 800, and red blood cells which are not the measurement target are lysed using a red blood cell lysis buffer and removed in advance. A cell inlet 308, a reagent inlet 305, an upper outlet 306 and a lower outlet 307 are the same as those in Example 1 (FIG. 2). In this Example, a pore array sheet prepared using a semiconductor process is used and is configured such that in order to arrange white blood cells in a square lattice using the flow of a solution from the cell inlet 308 to the lower outlet 307, a pore array is formed such that cells are sucked only in square regions, each having a side length of 15 μm, and the other region does not have pores, and also the thickness of the sheet is increased so as to maintain the mechanical strength of the device.

The pore array sheet used here was formed as follows. An $SiO_2$ layer having a thickness of 10 μm was formed on a silicon substrate 802, and through-holes having a diameter of 0.3 μm were formed using dry etching, and thereafter, the silicon substrate was thinned. Then, a lattice 803 with a pitch of 50 μm was formed by lithography, and the regions other than the lattice were pierced by wet etching. On the inner walls of the thus obtained pores, a DNA probe can be immobilized by a silane coupling treatment in the same manner as in Example 1. In FIG. 5C, a transverse sectional view taken along the line B-B' is shown, and different hatching patterns show that different cell recognition tag sequences are immobilized. Further, in FIG. 5B, a transverse sectional view taken along the line A-A' is shown. The regions 805 where through-pores are exposed are patterned to a size so as to house cells one by one.

FIG. 6 shows a case where separation of red blood cells is performed in a device. A pore array sheet is the same as that shown in FIG. 5 (a transverse sectional view taken along the line C-C' is shown in FIG. 6C), however, a cell filter 900 is provided on the upper portion thereof. A transverse sectional view above the cell filter 900 is shown in in FIG. 6B. As the size of the through-pore capable of allowing red blood cells to pass therethrough because of having a smaller size, and trapping white blood cells or CTC (Circulating Tumor Cell) on the filter 900 because of having a large size, 6 μm is selected.

Example 4

Figure 7A:
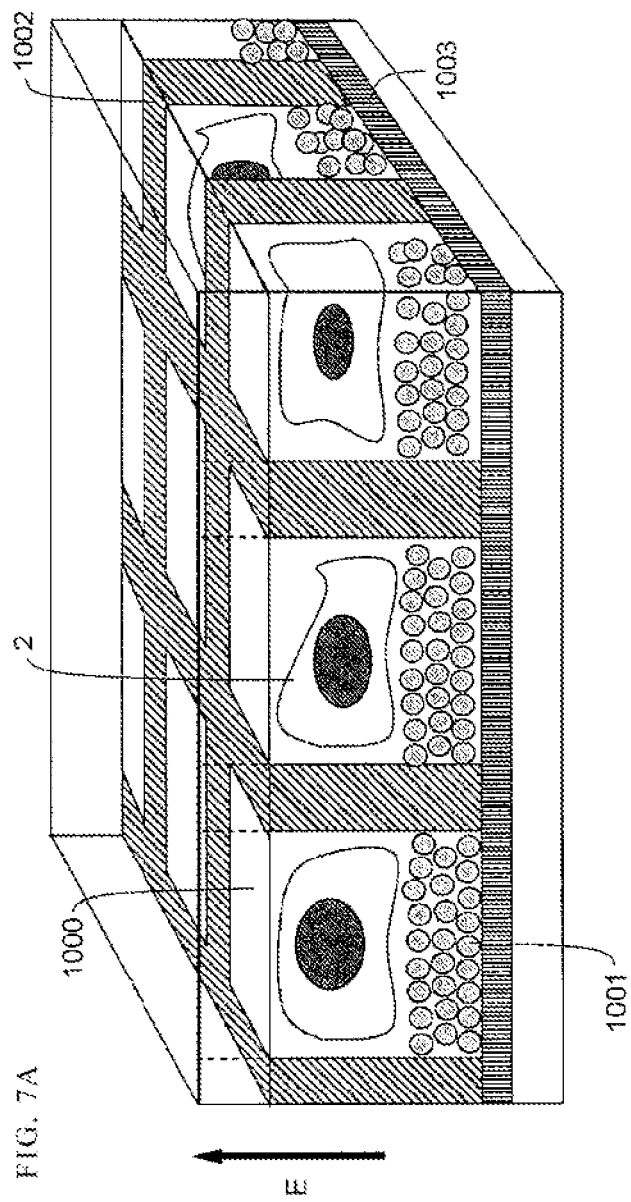
FIGS. 7A and 7B are views showing a configuration example of a device for gene expression analysis (beads) for constructing a cDNA library.

The device having a cDNA library constructed therein may be a device using beads other than a pore array sheet. In this case, it is not necessary to perform immobilization of the DNA probe on the device, and this device has an advantage that the DNA immobilization density is high. In FIG. 7A, a cross-sectional bird's eye view of only a device portion where a cDNA library array sheet is constructed is shown.

Figure 7B:
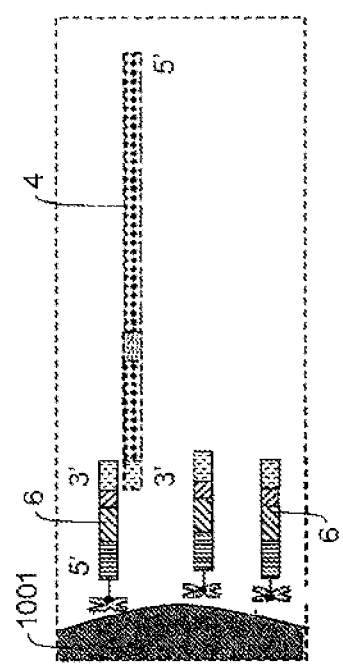

Reaction tanks 1000 having a side length of 10 μm are provided on the device, and magnetic beads 1001 (here, beads having streptavidin immobilized on the surface thereof in advance were used) having a diameter of 1 μm are filled therein. On the magnetic beads, a mRNA capture DNA probe 6 is immobilized, and this DNA probe includes, from the 5'-terminal side, a common sequence for PCR amplification (Forward direction), a cell recognition tag sequence, a molecule recognition tag sequence, and an oligo(dT) sequence. An enlarged view of the surface of the bead is shown in FIG. 7B. The cell recognition tag sequence of the mRNA capture DNA probe 6 immobilized on the bead is configured such that the sequence differs per position of the reaction tank on the device. Specifically, the mRNA capture DNA probes 6 having a different cell recognition tag sequence are mixed with beads 1001 in different reaction tubes, and a binding reaction is performed while rotating for 10 minutes. Thereafter, the beads 1001 having a different sequence immobilized thereon are separately filled in inkjet printer heads, and then, separately filled in the reaction tanks 1000.

The reaction tanks 1000, a mesh 1002 made of a resin, and a pore array sheet 1003 made of alumina also used in Example 1 were bonded to one another by heat fusion. Here, one having a pore diameter of 100 nm was used.

The mesh made of a resin was prepared by a nanoimprint technique, however, a commercially available nylon mesh or a track-etched membrane may be used. The reason why the bottom of the reaction tank is a mesh is because a solution can be made to pass therethrough, and the pore array made of alumina has high hydrophilicity, and therefore, the solution rapidly permeates the array.

Further, this reaction tanks 1000 may be integrally processed using a semiconductor process.

The number of beads 1001 in one reaction tank 1000 was set to 1000.

Such a device is disposed in a flow system provided with inlets and outlets as shown in FIG. 5A, and cells are introduced therein. A solution flows while permeating the beads and the pore array, and the cells are captured above the beads, and cell disruption with a cell-lysis reagent and extraction of mRNA by electrophoresis are simultaneously performed in the same manner as in Example 1, whereby mRNA 4 is captured on the magnetic beads 1001.

Example 5

This Example is an example of using a two-dimensional cDNA library sheet which was constructed in a pore array sheet, from a tissue section 1101.

Figure 8:
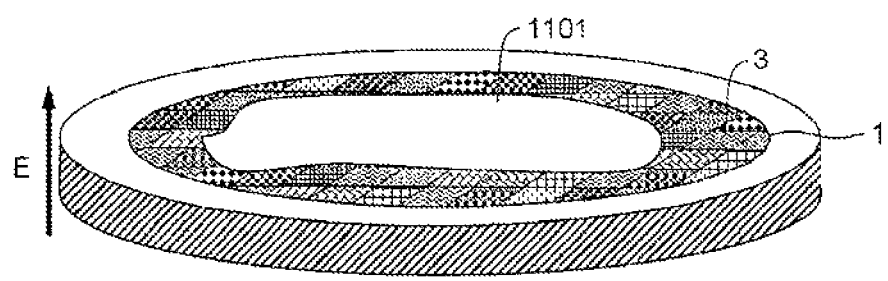
FIG. 8 is a schematic view showing a method for constructing a cDNA library in a device for gene expression analysis (a pore array sheet) from a tissue section.

A frozen tissue sample was formed into a film-shaped sample having a thickness of about 5 to 20 µm using a microtome, and as shown in FIG. 8, a tissue section 1101 is placed on a pore array sheet 1 made of alumina, and immediately thereafter, the tissue section is covered with low melting-point agarose containing a cell-lysis reagent. An agarose solution is maintained in a solution state at 35° C., and the sheet 1 is rapidly gelatinized by cooling it to 4° C. Thereafter, the sheet is set in the reaction cell shown in FIG. 2, and mRNA is extracted in the same manner as in Example 1.

At this time, the length of the cell recognition tag sequence of the mRNA capture DNA probe was changed to 10 bases so that even when up to 1,000,000 cells are present in the tissue section, these cells can be dicriminated, and the probe was ejected in an amount of 10 pL each by an inkjet printer at intervals of 10 µm.

Example 6

In the gene expression analysis using a two-dimensional cDNA library, the positions of cells on a planar device such as a pore array sheet and the results of gene expression analysis can be associated with each other. At this time, before performing detailed gene expression analysis by disrupting cells for gene expression analysis, measurement of the shape, quantitative determination of genes or proteins by fluorescence staining, or Raman imaging is performed in a state where cells are alive, and these imaging data and the gene expression analysis data can be associated with each other. A system configuration for realizing this will be described below.

Figure 9:
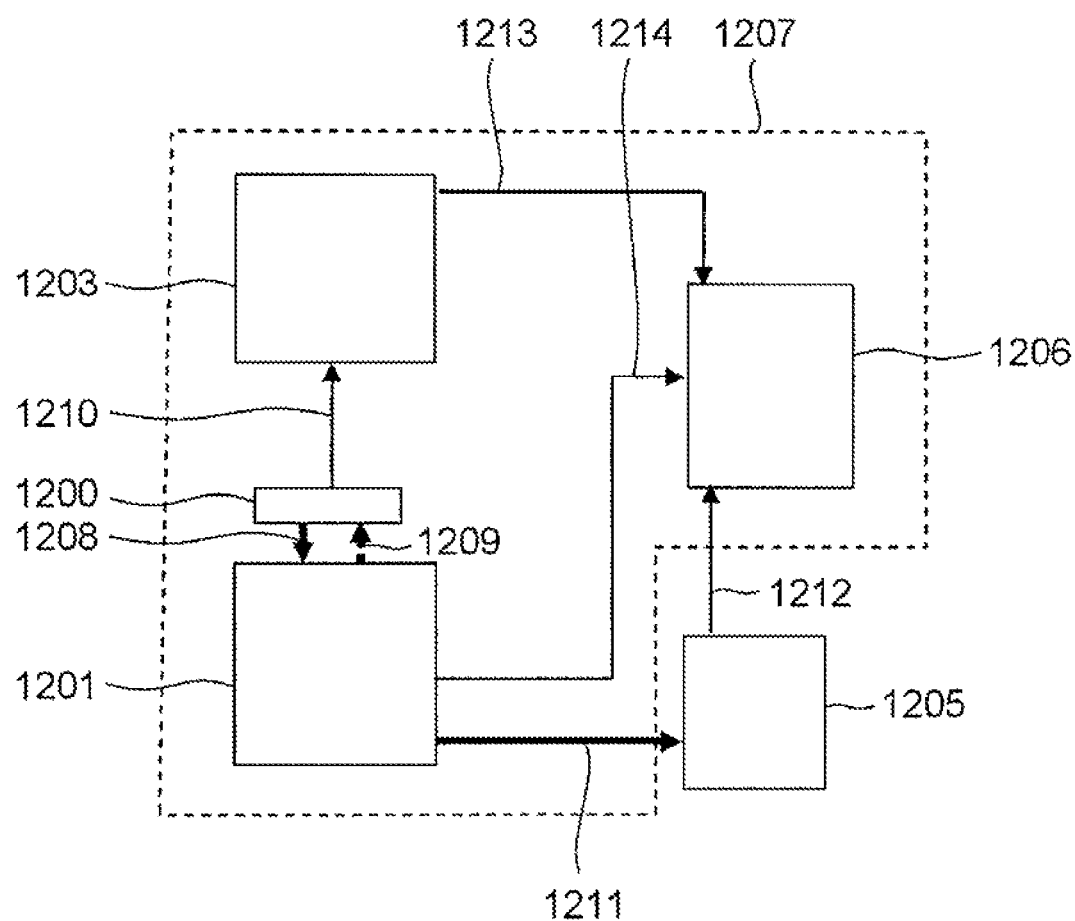
FIG. 9 is a view showing a configuration example of an apparatus for gene expression analysis of the invention.

First, FIG. 9 shows a system configuration for measuring the dynamics of cells in detail with respect to sample of cells disposed on a planar device (such as a pore array sheet) for constructing a two-dimensional cDNA library by associating the measurements by an optical microscope and the results of gene expression analysis using the device with the data of the respective cells.

Reference numeral 1200 denotes a planar device typified by a pore array sheet and a cell-sample disposed on the device before cell disruption. Reference numeral 1201 denotes a flow system (a reaction cell or a device) for performing mRNA extraction from cells and nucleic acid amplification typified by one shown in FIG. 2. An arrow 1208 shows a nucleic acid extraction process (the transfer of a substance is shown with a thick arrow). An arrow 1209 shows the addition of a cell-lysis reagent to cells or the addition of a reagent for a nucleic acid reaction thereafter. By controlling these, an amplification product having a given length and containing a tag sequence describing information before a nucleic acid treatment at an end can be obtained in a necessary amount for determining the sequence using a next generation (large-scale) DNA sequencer 1205. Also here, an arrow 1211 shows the transfer of the amplification product. On the other hand, the cell on the device is subjected to observation (1210) with a microscope 1203 while specifying the position of the cell on the device in advance. Here, a thin arrow shows the transfer of information. Examples of the microscope 1203 include a phase-contrast microscope, a differential interference microscope, a fluorescence microscope, a laser scanning confocal fluorescence microscope, a Raman microscope, a nonlinear Raman microscope (a CARS microscope, an SRS microscope, and an RIKE microscope), and an IR microscope. As far as gene information is concerned, the information obtained with these microscopes is little. However, basically, measurement in a state where cells are alive can be performed, and a change in cells over time can be measured, and also the response of cells to stimulation can be measured in real time. By utilizing the device storing the positional information on the device, detailed information related to gene expression and information containing changes over time obtained using a microscope can be associated with each other. In order to realize this, it is necessary to provide an information system 1206 that integrates sequence information 1212 from the next generation (large-scale) DNA sequencer, microscopic image information 1213, and positional information 1214 associated with the tag sequence within the system. In the invention, the minimum configuration of the system that integrates the measurement information of cells described above is a system 1207 which is a portion other than the next generation (large-scale) DNA sequencer 1205, and has input of information from the DNA sequencer and output of samples (nucleic acid amplification products).

Figure 10:
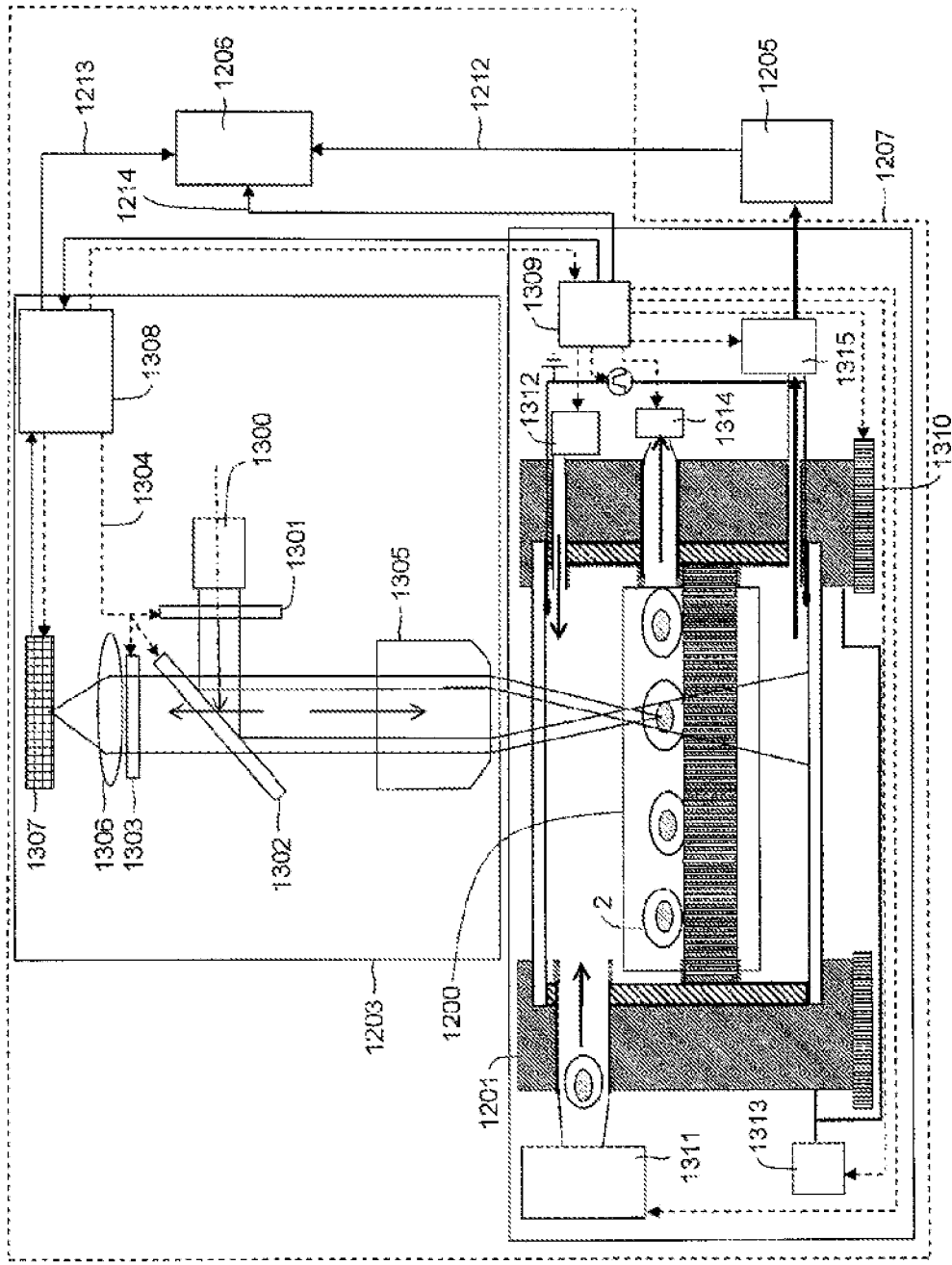
FIG. 10 is a view showing one example of a specific configuration of an apparatus for gene expression analysis of the invention.

FIG. 10 shows a configuration example of a system when a fluorescence microscope is combined as the microscope. In this example, reference numeral 1201 denotes a flow system, and reference numeral 1203 denotes a fluorescence microscope. A state where cells 2 are disposed on a pore array sheet 1 is shown. In the cells 2, GFP is expressed in a protein (for example, p53) to be measured or a fluorescent substance is introduced into a specific protein by immunostaining. The data of the protein expression level in the respective cells obtained in this manner can be correlated for each cell with the gene expression data obtained by a sample treatment on the pore array sheet 1 after cell disruption and quantitative determination by DNA sequencing. In order to recognize cells at this time, nucleic acids are stained with DAPI to recognize cell nuclei, whereby the positions of the cells are identified with a fluorescence microscope. Since the protein level is measured according to the expression of GFP, changes over time can be followed, however, the types of proteins which can be simultaneously measured are about several types. On the other hand, in gene expression analysis by sequencing, about 100 types can be measured at a time, and it is also possible to perform analysis of 1000 types if a necessary number of probes are prepared. Due to this, detailed information related to gene expression control in cells can be obtained for each individual cell. However, changes over time with respect to this cannot be detected. If data as to what gene expression pattern is like when what protein expression pattern is like are obtained in advance by combining both, it is possible to deduce information related to gene control only from the protein expression data. The association between the fluorescence microscopic data and the gene expression data, and the deduction of information related to gene control are performed by the information system 1206.

Next, the configuration of the fluorescence microscope 1203 will be described in detail. Reference numeral 1300 denotes a light source, and a mercury lamp is used here. Reference numeral 1301 denotes an excitation filter that determines an excitation wavelength, reference numeral 1302 denotes a dichroic mirror, and reference numeral 1303 denotes an emission filter that selects a received light wavelength. When multiple types of fluorescent substances are introduced into cells and measured simultaneously, the members denoted by 1301, 1302, and 1303 are selected by control 1304 so that only light from a specific fluorescent substance is measured. Fluorescence imaging of cells is performed with an objective lens 1305, an imaging lens 1306, and a CCD camera 1307. A control computer that performs control of these and acquires image data is denoted by reference numeral 1308.

Next, a control system of the flow system 1201 will be described. A control computer of the flow system is denoted by reference numeral 1309. This controls an XY stage 1310 to transfer a microscopic image. At this time, the control computer 1309 can associate the position coordinate on the pore array sheet 1, the sequence data of the cell recognition tag sequence, and the position coordinate on the microscopic image calculated using the position coordinate on the XY stage. This control computer 1309 appropriately controls a cell-introduction control device 1311 that controls introduction of cells into a flow cell system, a reagent control device 1312 that controls introduction of a differentiation inducer for changing the state of cells, an agent for examining response of cells, a cell-lysis reagent for disrupting cells, or a reagent for a sample treatment, a temperature and $CO_2$ concentration control device 1313 that controls cell culture conditions or a thermal cycle during PCR, an upper reagent discharge device 1314 that is used for replacement of unnecessary reagents, cells, medium, or the like, and a lower reagent discharge device 1315 for discharging prepared nucleic acid amplification products. The finally obtained nucleic acid amplification products are transferred to the next generation (large-scale) DNA sequencing system 1205, and sequence analysis is performed. At this time, emPCR or bridge amplification for sequencing is supposed to be performed in this system. The positional information of an image collated on the control computer and the sequence information of the cell recognition tag sequence are sent to the integrated information system 1206 and associated with the protein level and the gene expression level obtained from the fluorescence image. Further, by the same system, changes over time of the gene expression analysis data are estimated. According to this, the dynamics of the gene expression network can be measured.

Further, this fluorescence microscope may be used not only for the measurement in cells, but also for the measurement of the amount of a substance secreted from cells such as cytokine which is introduced into a pore array sheet and captured by an antibody by immunofluorescence staining. Needless to say, the fluorescence microscope may be used in analysis of gene expression level after disruption.

Figure 11:
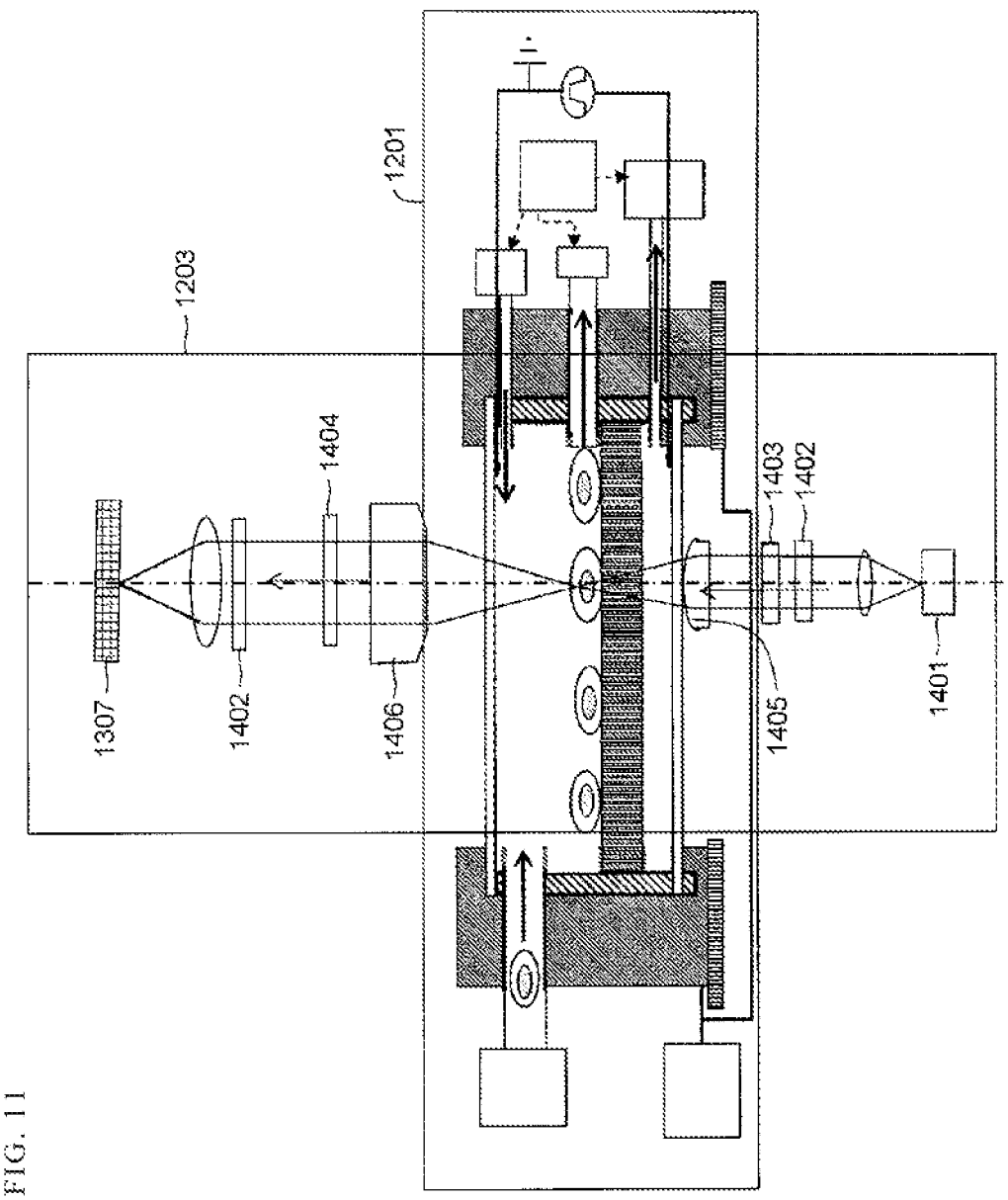
FIG. 11 is a view showing another example of a specific configuration of the apparatus for gene expression analysis of the invention.

FIG. 11 shows an example of combining a differential interference microscope 1203 as the microscope. A differential interference microscopic image is used only for measuring the shape without using a fluorescent reagent, but is one of the measurement methods having the smallest influence on cells when the cells should be returned in the body in regenerative medicine or the like. In the case where changes in cell shape obtained from this image and changes in gene expression can be associated with each other, the system becomes a measurement system which can perform detailed cell classification with least damage to cells.

Reference numeral 1401 denotes a light source, and a halogen lamp is used here. Reference numeral 1402 denotes a polarizer, and reference numerals 1403 and 1404 denote a Wollaston filter and a Wollaston prism, respectively. Reference numeral 1405 denotes a condenser lens, and reference numeral 1406 denotes an objective lens.

Figure 12:
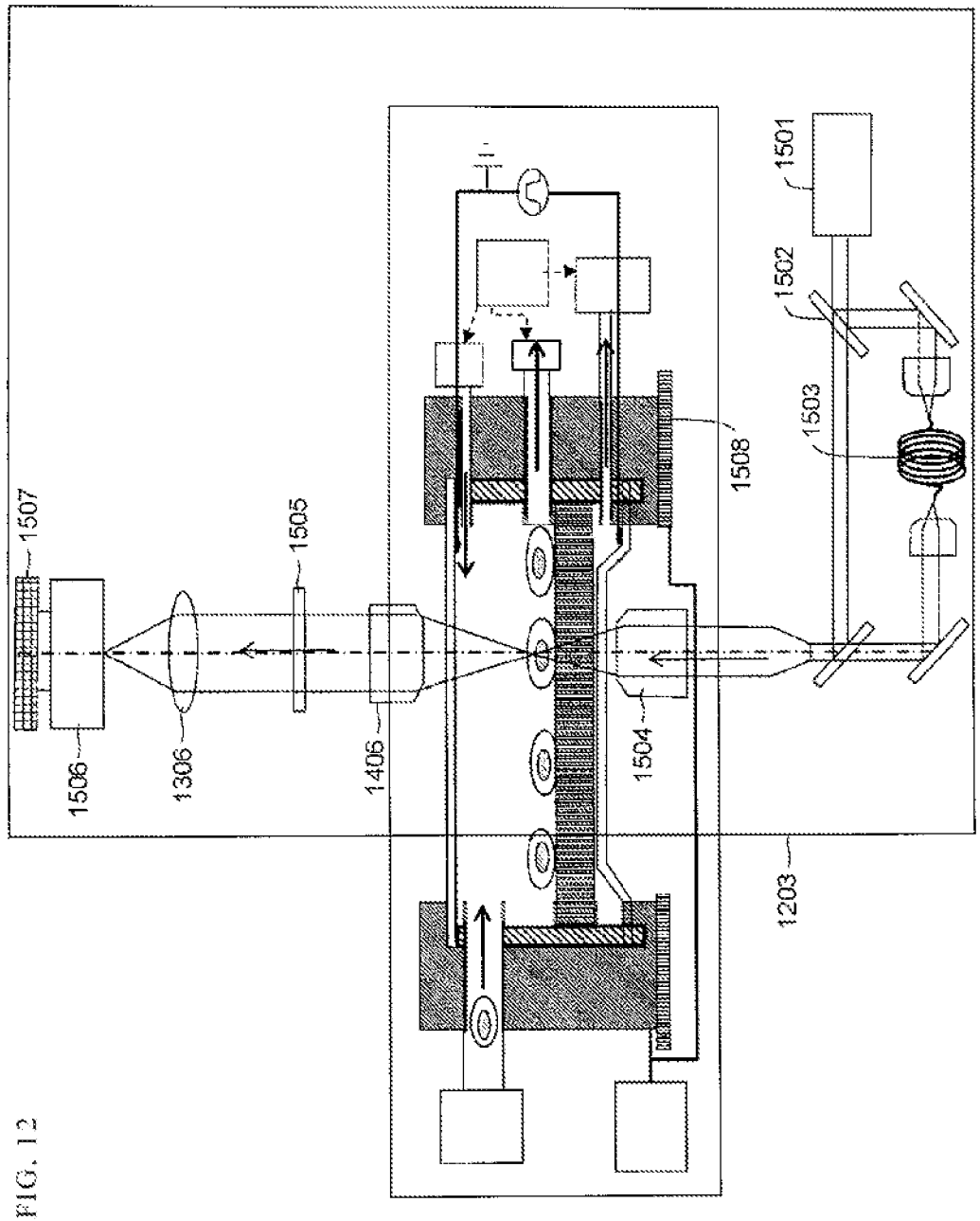
FIG. 12 is a view showing another example of a specific configuration of the apparatus for gene expression analysis of the invention.

FIG. 12 shows an example of using a CARS microscope 1203 as the microscope. By using the CARS microscope, a spectrum corresponding to a chemical species in a laser-excited region can be obtained in the same manner as a Raman microscope or an IR microscope, and therefore, the amount of information for cell states can be increased as compared with a differential interference microscope. However, CARS is a nonlinear process, and the signal intensity is higher than a Raman signal, and therefore, a sufficient signal can be obtained at a relatively low laser excitation intensity, and thus, it has an advantage that the damage to cells is low. By associating such a CARS image with the gene expression analysis data, a more detailed cell state can be determined.

Reference numeral 1501 denotes a light source, and a pulse laser (microchip laser) is used here. A laser is split into two components with a beam splitter 1502, and one component is introduced into a nonlinear fiber (photonic crystal fiber) 1503 to produce a Stokes beam. The other light component is directly used as a pump beam and a probe beam, and collected on a sample (in individual cells) with a water-immersion objective lens 1504 to produce an anti-Stokes beam. Only the anti-Stokes beam is transmitted with a high-pass filter 1505 and passed through a spectroscope 1506, and a coherent anti-Stokes Raman spectrum is obtained with a spectroscopic CCD camera 1507. The position where measurement is performed with the camera 1507 is scanned with a movable xyz stage 1508, and an xyz image is constructed.

Note that the present invention is not limited to the above-described embodiments, but includes various modifications. For example, the above-described embodiments have been described in detail so as to assist the understanding of the invention, and the invention is not always limited to embodiments having all the described constituent elements. Further, it is possible to replace a part of constituent elements of an embodiment with constituent elements of another embodiment, and it is also possible to add a constituent element of another embodiment to a constituent element of an embodiment. Further, regarding a part of a constituent element of each embodiment, it is possible to perform addition, deletion, or replacement using other constituent elements.

All publications, patents, and patent applications cited herein are hereby incorporated by reference in their entirety.

REFERENCE SINGS LIST

1: pore array sheet
2: cell

300: protection ring
301: upper cover, upper electrode
302: lower cover, lower electrode
303: upper reaction region
304: lower reaction region
305: inlet
306: upper outlet
307: lower outlet
308: inlet
309: heat block
310: temperature controller
311: power source
800: white blood cell
802: silicon substrate
803: lattice
805: region where through-pore is exposed
900: cell filter
1000: reaction tank
1001: magnetic bead
1002: mesh
1003: pore array sheet
1200: planar device and cell sample disposed on the device
1201: flow system
1203: microscope
1205: DNA sequencer (DNA sequencing system)
1206: information system
1207: minimum configuration of system
1300: light source
1301: excitation filter
1302: dichroic mirror
1303: emission filter
1305: objective lens
1306: imaging lens
1307: CCD camera
1308: control computer
1309: control computer
1310: XY stage
1311: cell introduction control device
1312: reagent control device
1313: temperature and $CO_2$ concentration control device
1314: upper reagent discharge device
1315: lower reagent discharge device
1401: light source
1402: polarizer
1403: Wollaston filter
1404: Wollaston prism
1405: condenser lens
1406: objective lens
1501: light source
1502: beam splitter
1503: nonlinear fiber (photonic crystal fiber)
1504: water-immersion objective lens
1505: high-pass filter
1506: spectroscope
1507: spectroscopic CCD camera
1508: movable xyz stage

SEQUENCE LISTING FREE TEXT

SEQ ID NOS: 1 to 29: Artificial (DNA probe, primers, and random sequences)

SEQUENCE LISTING

PH-5278PCT Sequence Listing.txt

The invention claimed is:

1. A gene expression analysis method, comprising:
a step of hybridizing a test nucleic acid to serve as a target to a nucleic acid probe in a support
wherein the support is a substrate through which a large number of pores penetrate,
wherein the interval between the pores is the size corresponding to a single cell or smaller than the size of a single cell,
wherein the nucleic acid probe is immobilized on an inner surface of the pores which penetrate the support, and
wherein the nucleic acid probe comprises:
(a) a test nucleic acid capture sequence at its 3' terminal side, wherein the test nucleic acid capture sequence is capable of hybridizing the test nucleic acid;
(b) a molecule recognition tag sequence, wherein the molecule recognition tag sequence has a known or unknown sequence of 5 to 30 bases to recognize the same test nucleic acid from a cell captured by the test nucleic acid capture sequence by collecting the same molecule recognition tag sequence in the sequencing data for the amplified product from the test nucleic acid captured by the test nucleic acid capture sequence;
(c) a cell recognition tag sequence, wherein the cell recognition tag sequence has a known sequence of 5 to 30 bases and differs depending on the difference in position in the pores whose planar location on the support is known in relation to the sequence of the cell recognition tag sequence; and
(d) a common primer sequence for amplification;
a step of synthesizing a complementary DNA strand to the test nucleic acid, thereby preparing a cDNA library constituted by the DNA complementary strand containing the tag sequence; and
a step of performing nucleic acid amplification of the whole or part of the cDNA library.

2. The method according to claim 1, wherein the test nucleic acid to serve as a target is mRNA in individual cells constituting a biological tissue, and the cell recognition tag sequence is made to include a sequence which differs per region smaller than the size of the cell, whereby the cDNA library is prepared while keeping the in-plane positional information of the cell constituting the biological tissue.

3. The method according to claim 2, wherein the biological tissue is a tissue section, and mRNA in individual cells constituting the tissue section is transferred to the support in which a nucleic acid probe containing a cell recognition tag sequence which differs per region is immobilized.

4. The method according to claim 1, wherein the test nucleic acid to serve as a target is mRNA in multiple cells arranged in an array retained two-dimensionally, and the cell recognition tag sequence is made to include a sequence which differs per cell, whereby the cDNA library is prepared while keeping the positional information of the multiple cells.

5. The method according to claim 1, wherein the nucleic acid probe further contains a transcription factor promoter sequence, and the nucleic acid amplification step includes a transcription reaction from a cDNA to a cRNA using the transcription factor.

6. The method according to claim 1, further comprising a step of sequencing the amplified product.

* * * * *

```
                        SEQUENCE LISTING

<160> NUMBER OF SEQ ID NOS: 29

<210> SEQ ID NO 1
<211> LENGTH: 70
<212> TYPE: DNA
<213> ORGANISM: Artificial
<220> FEATURE:
<223> OTHER INFORMATION: DNA probe
<220> FEATURE:
<221> NAME/KEY: misc_feature
<222> LOCATION: (36)..(50)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 1
ccatctcatc cctgcgtgtc tccgactcag agctannnnn nnnnnnnnnn tttttttttt    60 ttttttttvn                                                          70

<210> SEQ ID NO 2
<211> LENGTH: 23
<212> TYPE: DNA
<213> ORGANISM: Artificial Sequence
<220> FEATURE:
<223> OTHER INFORMATION: Common sequence for PCR amplification, Reverse

<400> SEQUENCE: 2
cctctctatg ggcagtcggt gat                                           23
```

```
<210> SEQ ID NO 3
<211> LENGTH: 45
<212> TYPE: DNA
<213> ORGANISM: Artificial Sequence
<220> FEATURE:
<223> OTHER INFORMATION: Primer for 2nd cDNA strand synthesis of ATP5B
      gene

<400> SEQUENCE: 3
cctctctatg ggcagtcggt gatccctaac ccaaaaagct tcatt              45

<210> SEQ ID NO 4
<211> LENGTH: 45
<212> TYPE: DNA
<213> ORGANISM: Artificial Sequence
<220> FEATURE:
<223> OTHER INFORMATION: Primer for 2nd cDNA strand synthesis of GAPDH
      gene

<400> SEQUENCE: 4
cctctctatg ggcagtcggt gatcactgaa tctcccctcc tcaca              45

<210> SEQ ID NO 5
<211> LENGTH: 43
<212> TYPE: DNA
<213> ORGANISM: Artificial Sequence
<220> FEATURE:
<223> OTHER INFORMATION: Primer for 2nd cDNA strand synthesis of GUSB
      gene

<400> SEQUENCE: 5
cctctctatg ggcagtcggt gatcgtttct ggcctgggtt ttg                43

<210> SEQ ID NO 6
<211> LENGTH: 43
<212> TYPE: DNA
<213> ORGANISM: Artificial Sequence
<220> FEATURE:
<223> OTHER INFORMATION: Primer for 2nd cDNA strand synthesis of HMBS
      gene

<400> SEQUENCE: 6
cctctctatg ggcagtcggt gatgatgact gccttgcctc ctc                43

<210> SEQ ID NO 7
<211> LENGTH: 48
<212> TYPE: DNA
<213> ORGANISM: Artificial Sequence
<220> FEATURE:
<223> OTHER INFORMATION: Primer for 2nd cDNA strand synthesis of HPRT1
      gene

<400> SEQUENCE: 7
cctctctatg ggcagtcggt gattagtagt gtttcagtaa tgttgact           48

<210> SEQ ID NO 8
<211> LENGTH: 43
<212> TYPE: DNA
<213> ORGANISM: Artificial Sequence
<220> FEATURE:
<223> OTHER INFORMATION: Primer for 2nd cDNA strand synthesis of RPL4
      gene

<400> SEQUENCE: 8
cctctctatg ggcagtcggt gataagaagc tgctgcata aac                 43
```

-continued

<210> SEQ ID NO 9
<211> LENGTH: 49
<212> TYPE: DNA
<213> ORGANISM: Artificial Sequence
<220> FEATURE:
<223> OTHER INFORMATION: Primer for 2nd cDNA strand synthesis of RPLP1
      gene

<400> SEQUENCE: 9
cctctctatg ggcagtcggt gataagtgga agcaaagaaa gaagaatcc                49

<210> SEQ ID NO 10
<211> LENGTH: 41
<212> TYPE: DNA
<213> ORGANISM: Artificial Sequence
<220> FEATURE:
<223> OTHER INFORMATION: Primer for 2nd cDNA strand synthesis of RPS18
      gene

<400> SEQUENCE: 10
cctctctatg ggcagtcggt gatgtgtccg aggccagcac a                        41

<210> SEQ ID NO 11
<211> LENGTH: 48
<212> TYPE: DNA
<213> ORGANISM: Artificial Sequence
<220> FEATURE:
<223> OTHER INFORMATION: Primer for 2nd cDNA strand synthesis of RPL13A
      gene

<400> SEQUENCE: 11
cctctctatg ggcagtcggt gattctagaa gcagaaatag actgggaa                 48

<210> SEQ ID NO 12
<211> LENGTH: 48
<212> TYPE: DNA
<213> ORGANISM: Artificial Sequence
<220> FEATURE:
<223> OTHER INFORMATION: Primer for 2nd cDNA strand synthesis of RPS20
      gene

<400> SEQUENCE: 12
cctctctatg ggcagtcggt gatgagattg ttaagcagat tacttcca                 48

<210> SEQ ID NO 13
<211> LENGTH: 42
<212> TYPE: DNA
<213> ORGANISM: Artificial Sequence
<220> FEATURE:
<223> OTHER INFORMATION: Primer for 2nd cDNA strand synthesis of ALDOA
      gene

<400> SEQUENCE: 13
cctctctatg ggcagtcggt gatttgcccg cgctctttct tc                       42

<210> SEQ ID NO 14
<211> LENGTH: 50
<212> TYPE: DNA
<213> ORGANISM: Artificial Sequence
<220> FEATURE:
<223> OTHER INFORMATION: Primer for 2nd cDNA strand synthesis of B2M
      gene

<400> SEQUENCE: 14
cctctctatg ggcagtcggt gatattcata tttacttctt atacatttga               50

```
<210> SEQ ID NO 15
<211> LENGTH: 43
<212> TYPE: DNA
<213> ORGANISM: Artificial Sequence
<220> FEATURE:
<223> OTHER INFORMATION: Primer for 2nd cDNA strand synthesis of EEF1G
      gene

<400> SEQUENCE: 15
cctctctatg ggcagtcggt gataaagcct tcaatcaggg caa            43

<210> SEQ ID NO 16
<211> LENGTH: 41
<212> TYPE: DNA
<213> ORGANISM: Artificial Sequence
<220> FEATURE:
<223> OTHER INFORMATION: Primer for 2nd cDNA strand synthesis of SDHA
      gene

<400> SEQUENCE: 16
cctctctatg ggcagtcggt gatccaggga gcgtggcact t              41

<210> SEQ ID NO 17
<211> LENGTH: 43
<212> TYPE: DNA
<213> ORGANISM: Artificial Sequence
<220> FEATURE:
<223> OTHER INFORMATION: Primer for 2nd cDNA strand synthesis of TBP
      gene

<400> SEQUENCE: 17
cctctctatg ggcagtcggt gatctccagt attgcaggac aga            43

<210> SEQ ID NO 18
<211> LENGTH: 43
<212> TYPE: DNA
<213> ORGANISM: Artificial Sequence
<220> FEATURE:
<223> OTHER INFORMATION: Primer for 2nd cDNA strand synthesis of VIM
      gene

<400> SEQUENCE: 18
cctctctatg ggcagtcggt gataatcttg tgctagaata ctt            43

<210> SEQ ID NO 19
<211> LENGTH: 43
<212> TYPE: DNA
<213> ORGANISM: Artificial Sequence
<220> FEATURE:
<223> OTHER INFORMATION: Primer for 2nd cDNA strand synthesis of RPLP0
      gene

<400> SEQUENCE: 19
cctctctatg ggcagtcggt gattcggacg aggatatggg att            43

<210> SEQ ID NO 20
<211> LENGTH: 44
<212> TYPE: DNA
<213> ORGANISM: Artificial Sequence
<220> FEATURE:
<223> OTHER INFORMATION: Primer for 2nd cDNA strand synthesis of RPLP2
      gene

<400> SEQUENCE: 20
cctctctatg ggcagtcggt gatatgagaa gaaggaggag tctg           44
```

<210> SEQ ID NO 21
<211> LENGTH: 41
<212> TYPE: DNA
<213> ORGANISM: Artificial Sequence
<220> FEATURE:
<223> OTHER INFORMATION: Primer for 2nd cDNA strand synthesis of RPLP27 gene

<400> SEQUENCE: 21
cctctctatg ggcagtcggt gatgggaggc caaggtcaag t                41

<210> SEQ ID NO 22
<211> LENGTH: 45
<212> TYPE: DNA
<213> ORGANISM: Artificial Sequence
<220> FEATURE:
<223> OTHER INFORMATION: Primer for 2nd cDNA strand synthesis of OAZ1 gene

<400> SEQUENCE: 22
cctctctatg ggcagtcggt gatagaagtt tcttatttgg agtct            45

<210> SEQ ID NO 23
<211> LENGTH: 30
<212> TYPE: DNA
<213> ORGANISM: Artificial Sequence
<220> FEATURE:
<223> OTHER INFORMATION: Common sequence for PCR amplification, Forward

<400> SEQUENCE: 23
ccatctcatc cctgcgtgtc tccgactcag                             30

<210> SEQ ID NO 24
<211> LENGTH: 112
<212> TYPE: DNA
<213> ORGANISM: Artificial Sequence
<220> FEATURE:
<223> OTHER INFORMATION: DNA probe containing T7 promoter sequence
<220> FEATURE:
<221> NAME/KEY: misc_feature
<222> LOCATION: (78)..(92)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t

<400> SEQUENCE: 24
aaacgacggc cagtgaattg taatacgact cactataggc gcccatctca tccctgcgtg   60
tctccgactc agagctannn nnnnnnnnnn nntttttttt tttttttttt vn          112

<210> SEQ ID NO 25
<211> LENGTH: 15
<212> TYPE: DNA
<213> ORGANISM: Artificial Sequence
<220> FEATURE:
<223> OTHER INFORMATION: Random sequence

<400> SEQUENCE: 25
acgccgttat aattg                                             15

<210> SEQ ID NO 26
<211> LENGTH: 15
<212> TYPE: DNA
<213> ORGANISM: Artificial Sequence
<220> FEATURE:
<223> OTHER INFORMATION: Random sequence

```
<400> SEQUENCE: 26
atctcttact tctac                                                    15

<210> SEQ ID NO 27
<211> LENGTH: 15
<212> TYPE: DNA
<213> ORGANISM: Artificial Sequence
<220> FEATURE:
<223> OTHER INFORMATION: Random sequence

<400> SEQUENCE: 27
gctcctactc aatca                                                    15

<210> SEQ ID NO 28
<211> LENGTH: 15
<212> TYPE: DNA
<213> ORGANISM: Artificial Sequence
<220> FEATURE:
<223> OTHER INFORMATION: Random sequence

<400> SEQUENCE: 28
acccggtata cgtac                                                    15

<210> SEQ ID NO 29
<211> LENGTH: 15
<212> TYPE: DNA
<213> ORGANISM: Artificial Sequence
<220> FEATURE:
<223> OTHER INFORMATION: Random sequence

<400> SEQUENCE: 29
ttacctacta ctgga                                                    15
```